(12) United States Patent
De Windt et al.

(10) Patent No.: US 8,815,822 B2
(45) Date of Patent: Aug. 26, 2014

(54) MEANS AND METHODS FOR COUNTERACTING, DELAYING AND/OR PREVENTING ADVERSE ENERGY METABOLISM SWITCHES IN HEART DISEASE

(75) Inventors: Leon Johannes De Windt, Culemborg (NL); Hamid El Azzouzi, Nieuwegein (NL)

(73) Assignees: Universiteit Maastricht, Maastricht (NL); Academisch Ziekenhuis Maastricht, Maastricht (NL)

( * ) Notice: Subject to any disclaimer, the term of this patent is extended or adjusted under 35 U.S.C. 154(b) by 3 days.

(21) Appl. No.: 13/389,236

(22) PCT Filed: Aug. 6, 2009

(86) PCT No.: PCT/NL2009/050484
§ 371 (c)(1),
(2), (4) Date: Feb. 23, 2012

(87) PCT Pub. No.: WO2011/016714
PCT Pub. Date: Feb. 10, 2011

(65) Prior Publication Data
US 2012/0141442 A1 Jun. 7, 2012

(51) Int. Cl.
*C12N 15/113* (2010.01)
(52) U.S. Cl.
CPC ........ *C12N 15/113* (2013.01); *C12N 2310/113* (2013.01); *C12N 2310/141* (2013.01)
USPC .......................................... 514/44 A; 435/6.1
(58) Field of Classification Search
CPC .............................. C12N 15/113; C12N 15/11
USPC ........................... 514/44 A; 435/6.1; 536/24.5
See application file for complete search history.

(56) References Cited

U.S. PATENT DOCUMENTS

| 8,288,356 B2 * | 10/2012 | Obad et al. | 514/44 A |
| 2010/0010073 A1 * | 1/2010 | Thum et al. | 514/44 R |
| 2011/0086348 A1 * | 4/2011 | Prasad et al. | 435/6 |
| 2011/0152352 A1 * | 6/2011 | Hata et al. | 514/44 A |
| 2012/0165392 A1 * | 6/2012 | Olson et al. | 514/44 A |

FOREIGN PATENT DOCUMENTS

| WO | WO 2007/073737 A1 | 7/2007 |
| WO | WO 2011/016714 A1 | 2/2011 |

OTHER PUBLICATIONS

Sayed et al., Circ Res. Feb. 16, 2007;100(3):416-24. Epub Jan. 18, 2007. MicroRNAs play an essential role in the development of cardiac hypertrophy.*
van Rooij et al Proc Natl Acad Sci U S A. Nov. 28, 2006;103(48):18255-60. Epub Nov. 15, 2006.A signature pattern of stress-responsive microRNAs that can evoke cardiac hypertrophy and heart failure.*
Lee et al PPARdelta activation inhibits angiotensin II induced cardiomyocyte hypertrophy by suppressing intracellular Ca2+ signaling pathway. J Cell Biochem. Apr. 1, 2009;106(5):823-34.*
Lin et al., Febs J. Apr. 2009;276(8):2348-58.A role of miR-27 in the regulation of adipogenesis Abstract.*
Sayed et al., MicroRNAs play an Essential Role in the Development of Cardiac Hypertrophy, Circulation Research, Feb. 1, 2007, pp. 416-24, vol. 100, No. 3., Grune and Stratton, Baltimore, US.
Van Rooij et al., A Signature Pattern of Stress-Responsive microRNAs that Can Evoke Cardiac Hyperthrophy and Heart Failure, PNAS, Nov. 28, 2006, pp. 18255-60, vol. 103, No. 48.
Lee et al., PPARδ Activation Inhibits Angiotensin II Induced Cardiomyocyte Hypertrophy by Suppressing Intracelluar Ca2+ Signaling Pathway, J. Cell, Biochem, Feb. 17, 2009, pp. 823-34, vol. 106.
Cheng et al., MicroRNAs Are Aberrantly Expressed in Hypertrophic Heart, Amerc. J. Pathology, Jun. 6, 2007, pp. 1831-40, vol. 170, No. 6.
PCT International Search Report and Written Opinion, PCT/NL2009/050484, dated May 12, 2010.
El Azzouzi et al., The Hypoxia-Inducible MicroRNA Cluster miR-199a~214 Targets Myocardial PPARδ and Impairs Mitochondrial Fatty Acid Oxidation, Cell Metabolism, Sep. 3, 2013, pp. 341-54, vol. 18, Elsevier Inc.

* cited by examiner

*Primary Examiner* — Maria Leavitt
(74) *Attorney, Agent, or Firm* — TraskBritt, P.C.

(57) ABSTRACT

The invention relates to the fields of molecular biology and medicine, more specifically to treatment and prevention of heart disease. The invention provides alternative methods for counteracting, diminishing, treating, delaying and/or preventing heart disease.

7 Claims, 6 Drawing Sheets

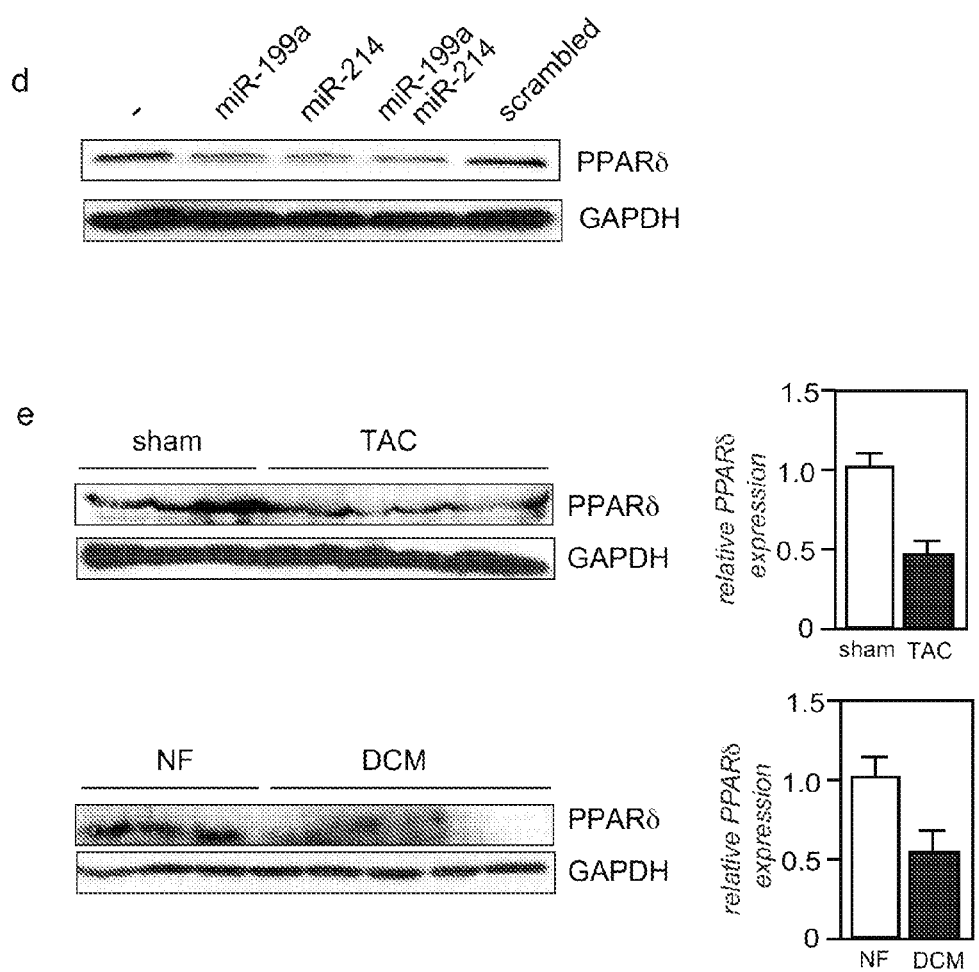
Figure 1, continued a hsa-miR-199a-5p sequence:

5'- CCCAGUGUUCAGACUACCUGUUC -3'

Antagomir capable of blocking hsa-miR-199a

5'- G*A*ACAGGUAGUCUGAACACU*G*G*G*Chol*T -3' b hsa-miR-214 sequence:

5'- ACAGCAGGCACAGACAGGCAGU -3'

Antagomir capable of blocking hsa-miR-214

5'- A*C*UGCCUGUCUGUGCCUGC*U*G*U*Chol*T -3'

```
                              SEQUENCE LISTING

<160> NUMBER OF SEQ ID NOS: 21

<210> SEQ ID NO 1
<211> LENGTH: 23
<212> TYPE: RNA
<213> ORGANISM: Artificial
<220> FEATURE:
<223> OTHER INFORMATION: hsa-miR-199a-5p

<400> SEQUENCE: 1
cccaguguuc agacuaccug uuc                                              23

<210> SEQ ID NO 2
<211> LENGTH: 22
<212> TYPE: RNA
<213> ORGANISM: Artificial
<220> FEATURE:
<223> OTHER INFORMATION: hsa-miR-199a-3p

<400> SEQUENCE: 2
acaguagucu gcacauuggu ua                                               22

<210> SEQ ID NO 3
<211> LENGTH: 22
<212> TYPE: RNA
<213> ORGANISM: Artificial
<220> FEATURE:
<223> OTHER INFORMATION: hsa-miR-214

<400> SEQUENCE: 3
acagcaggca cagacaggca gu                                               22

<210> SEQ ID NO 4
<211> LENGTH: 22
<212> TYPE: RNA
<213> ORGANISM: Artificial
<220> FEATURE:
<223> OTHER INFORMATION: hsa-miR-214*

<400> SEQUENCE: 4
```
ugccugucua cacuugcugu gc                                    22

<210> SEQ ID NO 5
<211> LENGTH: 22
<212> TYPE: DNA
<213> ORGANISM: Artificial
<220> FEATURE:
<223> OTHER INFORMATION: Primer

<400> SEQUENCE: 5
aggccgcagc ccaggcctcc cc                                    22

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
ctgggaatat ggctcccggc c                                     21

<210> SEQ ID NO 7
<211> LENGTH: 31
<212> TYPE: RNA
<213> ORGANISM: Artificial
<220> FEATURE:
<223> OTHER INFORMATION: miR-199a-5p

<400> SEQUENCE: 7
gccccagugu ucagacuacc uguucaggac a                          31

<210> SEQ ID NO 8
<211> LENGTH: 32
<212> TYPE: RNA
<213> ORGANISM: Artificial
<220> FEATURE:
<223> OTHER INFORMATION: miR-199a-3p

<400> SEQUENCE: 8 auggguugu acaguagucu gcacauuggu ua                          32

<210> SEQ ID NO 9
<211> LENGTH: 35
<212> TYPE: RNA
<213> ORGANISM: Artificial
<220> FEATURE:
<223> OTHER INFORMATION: miR-214

<400> SEQUENCE: 9
cgcucacugu acagcaggca cagacaggca gucac                      35

<210> SEQ ID NO 10
<211> LENGTH: 35
<212> TYPE: RNA
<213> ORGANISM: Artificial
<220> FEATURE:
<223> OTHER INFORMATION: miR-214*

<400> SEQUENCE: 10
gugucugccu gucuacacuu gcugugcaga acauc                      35

<210> SEQ ID NO 11
<211> LENGTH: 10
<212> TYPE: RNA
<213> ORGANISM: Artificial

```
<220> FEATURE:
<223> OTHER INFORMATION: hsa-miR-199a-2 3' fragment

<400> SEQUENCE: 11
ucagacuacc                                                            10

<210> SEQ ID NO 12
<211> LENGTH: 18
<212> TYPE: RNA
<213> ORGANISM: Artificial
<220> FEATURE:
<223> OTHER INFORMATION: hsa-miR-199a-2

<400> SEQUENCE: 12
cccaguguuc agacuacc                                                   18

<210> SEQ ID NO 13
<211> LENGTH: 15
<212> TYPE: RNA
<213> ORGANISM: Homo sapiens

<400> SEQUENCE: 13
ggggccagca cugga                                                      15

<210> SEQ ID NO 14
<211> LENGTH: 15
<212> TYPE: RNA
<213> ORGANISM: Mus musculus

<400> SEQUENCE: 14
ggggccugca cuggc                                                      15

<210> SEQ ID NO 15
<211> LENGTH: 15
<212> TYPE: RNA
<213> ORGANISM: Artificial
<220> FEATURE:
<223> OTHER INFORMATION: hsa-miR-214

<400> SEQUENCE: 15
acagcaggca cagac                                                      15

<210> SEQ ID NO 16
<211> LENGTH: 16
<212> TYPE: RNA
<213> ORGANISM: Homo sapiens

<400> SEQUENCE: 16
gucaugggcc ugcugc                                                     16

<210> SEQ ID NO 17
<211> LENGTH: 13
<212> TYPE: RNA
<213> ORGANISM: Mus musculus

<400> SEQUENCE: 17
ucaggccugc ugc                                                        13

<210> SEQ ID NO 18
<211> LENGTH: 23
<212> TYPE: RNA
<213> ORGANISM: Artificial
<220> FEATURE:
<223> OTHER INFORMATION: Antagomir capable of blocking hsa-miR-199a
<220> FEATURE:
```

```
<221> NAME/KEY: misc_structure
<222> LOCATION: (23)..(23)
<223> OTHER INFORMATION: The "g" at position 23 is attached to
      cholesterol triethyleneglycol via a hydroxylprolinol linkage

<400> SEQUENCE: 18
gaacagguag ucugaacacu ggg                                          23

<210> SEQ ID NO 19
<211> LENGTH: 22
<212> TYPE: RNA
<213> ORGANISM: Artificial
<220> FEATURE:
<223> OTHER INFORMATION: antagomir capable of blocking hsa-miR-214
<220> FEATURE:
<221> NAME/KEY: misc_structure
<222> LOCATION: (22)..(22)
<223> OTHER INFORMATION: The "u" at position 22 is attached to
      cholesterol triethyleneglycol via a hydroxylprolinol linkage

<400> SEQUENCE: 19
acugccuguc ugugccugcu gu                                           22

<210> SEQ ID NO 20
<211> LENGTH: 63
<212> TYPE: RNA
<213> ORGANISM: Artificial
<220> FEATURE:
<223> OTHER INFORMATION: Hairpin consturcuted from miR-199a-5p and
      miR-199a-3p

<400> SEQUENCE: 20
gccccagugu ucagacuacc uguucaggac aauggguug uacaguaguc ugcacauugg    60
uua                                                                63

<210> SEQ ID NO 21
<211> LENGTH: 70
<212> TYPE: RNA
<213> ORGANISM: Artificial
<220> FEATURE:
<223> OTHER INFORMATION: hairpin constructed from miR-214 adn miR-241*

<400> SEQUENCE: 21
cgcucacugu acagcaggca cagacaggca gucacgugu ugccugucua cacuugcugu    60
gcagaacauc                                                         70
```

MEANS AND METHODS FOR COUNTERACTING, DELAYING AND/OR PREVENTING ADVERSE ENERGY METABOLISM SWITCHES IN HEART DISEASE

CROSS-REFERENCE TO RELATED APPLICATION

This is a national phase entry under 35 U.S.C. §371 of International Patent Application PCT/NL2009/050484, filed Aug. 6, 2009, published in English as International Patent Publication WO 2011/016714 A1 on Feb. 10, 2011.

TECHNICAL FIELD

The invention relates to the fields of molecular biology and medicine, more specifically to treatment, delay and prevention of heart disease.

BACKGROUND

Heart disease, also called "cardiovascular disease," is a broad term used to describe a range of diseases that affect the heart and/or blood vessels. The conditions include coronary artery disease, heart attack, high blood pressure, stroke and heart failure. Cardiovascular disease is the No. 1 worldwide killer of men and women; e.g., in the U.S. it is responsible for 40 percent of all deaths, more than all forms of cancer combined.

A common form of cardiovascular disease is coronary artery disease, which affects the arteries that supply the heart muscle with blood. Sometimes known as "CAD," coronary artery disease is the leading cause of heart attacks. It generally means that blood flow through the coronary arteries has become obstructed, reducing blood flow to the heart muscle. The most common cause of such obstructions is a condition called atherosclerosis, a largely preventable type of vascular disease. Coronary artery disease and the resulting reduced blood flow to the heart muscle can lead to other heart problems, such as chest pain (angina) and heart attack (myocardial infarction).

A heart attack is an injury to the heart muscle caused by a loss of blood supply. The medical term for heart attack is "myocardial infarction," often abbreviated MI. A heart attack usually occurs when a blood clot blocks the flow of blood through a coronary artery—a blood vessel that feeds blood to a part of the heart muscle. Interrupted blood flow to a heart can damage or destroy a part of the heart muscle.

A heart disease that affects the heart muscle itself is called a "cardiomyopathy." Some types of cardiomyopathy are genetic, while others occur for reasons that are less well understood. Types of cardiomyopathy include ischemic, which is caused by loss of heart muscle from reduced coronary blood flow; dilated, which means the heart chambers are enlarged; hypertrophic, which means the heart muscle is thickened; and idiopathic, which means the cause is unknown. One of the most common types of cardiomyopathy is idiopathic dilated cardiomyopathy—an enlarged heart without a known cause.

Heart disease can be either acquired (later in life) or congenital. Congenital heart disease refers to a form of heart disease that develops before birth (congenital). Congenital heart disease is a broad term and includes a wide range of diseases and conditions. These diseases can affect the formation of the heart muscle or its chambers or valves. They include such conditions as narrowing of a section of the aorta (coarctation) or holes in the heart (atrial or ventricular septal defect). Some congenital heart defects may be apparent at birth, while others may not be detected until later in life.

Next to the heart muscle itself, heart disease can also affect other structure, such as the heart valves. Four valves within the heart keep blood flowing in the right direction. Valves may be damaged by a variety of conditions leading to narrowing (stenosis), leaking (regurgitation or insufficiency) or improper closing (prolapse). Valvular disease may either be congenital, or the valves may be damaged by such conditions as rheumatic fever, infections (infectious endocarditis), connective tissue disorders, and certain medications or radiation treatments for cancer.

Heart rhythm problems (arrhythmias) occur when the electrical impulses in a heart that coordinate heartbeats do not function properly, causing the heart to beat too fast, too slow or irregularly. Other forms of cardiovascular disease can indirectly cause arrhythmias.

Perhaps the most common form of cardiovascular disease in the Western world, affecting about one in four Americans, is high blood pressure (hypertension), which means that the blood is pumped with excessive force through the blood vessels. Although potentially life threatening, it is one of the most preventable and treatable types of cardiovascular disease. High blood pressure also causes many other types of cardiovascular disease, such as stroke and heart failure.

Heart failure, a progressive disorder in which damage to the heart causes weakening of the cardiovascular system, can result from any of the before-mentioned structural or functional cardiac disorders. It manifests by fluid congestion or inadequate blood flow to tissues as a result of the heart's inability to fill with or pump a sufficient amount of blood through the body.

Depending on the side of the heart affected, the symptoms can be diverse and diagnosis is impossible on symptoms alone. Left-sided heart failure results in congestion of the lung veins and symptoms that reflect this, as well as poor circulation to the body, whereas right-sided heart failure presents with, e.g., peripheral edema and nocturia.

Heart failure may result from one or the sum of many causes. Many affect both sides, such as ischemic heart disease, chronic arrhythmias, cardiomyopathy, cardiac fibrosis, chronic severe anemia, and thyroid disease, whereas others, such as hypertension, aortic and mitral valve disease and coarctation, mainly cause left-sided heart failure and pulmonary hypertension and pulmonary or tricuspid valve disease often result in right-sided heart failure.

These causes of heart failure have in common that they all reduce the efficiency of the myocardium, or heart muscle, through damage or overloading. Over time, the resulting increase in workload will produce changes to the heart itself, which, for instance, include reduced contractility, a reduced stroke volume, reduced spare capacity, increased heart rate, hypertrophy of the myocardium and/or enlargement of the ventricles. These changes of the heart result in reduced cardiac output and increased strain on the heart, which increases the risk of cardiac arrest and reduces blood supply to the rest of the body.

Current treatment of heart failure focuses on treating the symptoms and signs and preventing the progression of the disease. Treatment includes exercise, eating healthy foods, reduction in salty foods, and abstinence from smoking and drinking alcohol. Further, pharmacological management can be applied focused on relieving symptoms, maintaining a euvolemic state, and delaying progression of heart failure.

Drugs used include: diuretic agents, vasodilator agents, positive inotropes, ACE inhibitors, beta blockers, and aldosterone antagonists.

Heart failure is a serious disorder that carries a reduced life expectancy. Many forms of heart failure can be controlled with medication, lifestyle change, and correction of any underlying disorder. However, heart failure is usually a chronic illness, and it may worsen with infection or other physical stressors. There is no real cure for heart failure.

Therefore, there is an unmet need for alternative treatments for heart failure and heart disease in general.

DISCLOSURE

An object of the present invention is to provide an alternative treatment for, and/or at least partial prevention of, heart disease.

Accordingly, the present invention provides alternative means and methods for counteracting, diminishing, treating, delaying and/or preventing heart disease.

In one embodiment, the invention provides a method for diminishing, counteracting, treating, delaying and/or preventing heart disease, comprising counteracting the expression, amount and/or activity of microRNA in a cell.

MicroRNAs (miRNAs) are small RNA molecules encoded in the genomes of plants and animals. These highly conserved, ~21-mer RNAs usually regulate the expression of genes by binding to the 3'-untranslated regions (3'-UTRs) of specific mRNAs. Each miRNA is thought to regulate multiple genes, and since hundreds of miRNA genes are predicted to be present in higher eukaryotes, the potential regulatory circuitry afforded by miRNA is enormous. Several research groups have provided evidence that miRNAs may act as key regulators of processes as diverse as early development, cell proliferation and cell death, apoptosis and fat metabolism, and cell differentiation. Recent studies of miRNA expression implicate miRNAs in brain development, chronic lymphocytic leukemia, colonic adenocarcinoma, Burkitt's Lymphoma, and viral infection suggesting possible links between miRNAs and viral disease, neurodevelopment, and cancer. There is speculation that in higher eukaryotes, the role of miRNAs in regulating gene expression could be as important as that of transcription factors.

Aberrant expression of miRNA, be it under- or overexpression, can result in many kinds of disorders. Recently many different miRNA were identified that relate to specific diseases. As many miRNAs, however, regulate several hundreds of genes, for most miRNA-related diseases, it is hitherto unknown which gene is regulated by the identified miRNA and is ultimately responsible for the disease. For instance, Sayed et al. (*Circ. Res.* 2007; 100:416-424) have identified, amongst others, that several miRNAs show increased or decreased expression during cardiac hypertrophy. The most prominent up-regulated miRNA are miR-199a, miR-199a*, miR-21 and miR-214. Up to the present invention, however, it was not known which genes may be deregulated by the aberrant expression of these miRNAs and whether up-regulation or down-regulation of any of these miRNAs cause heart disease or are, for instance, only a result of heart disease.

The present invention provides for the first time the insight that increased expression of miR-199a and/or miR-214 causes heart disease and that inhibiting these microRNA(s) inhibits cardiac hypertrophy. The present invention furthermore provides the insight that δ isoform of peroxisome proliferator activator receptor delta (PPARδ) is a direct target of miR-199a and/or miR-214. It is, for instance, shown that an increase in expression of miR-199a and/or miR-214 causes a down-regulation of PPARδ and that this down-regulation of PPARδ causes, amongst other things, a change in energy metabolism of myocardial cells, which is a hallmark feature of heart failure.

Previous work has demonstrated that PPARδ is involved in lipid metabolism, in embryo implantation and in the regulation of cell proliferation. It was also reported that PPARδ prostacyclin receptor activity is involved in cell-substrate adhesion, keratinocyte migration, and wound healing. PPARδ has protein heterodimerization activity and retinoid X receptor binding activity. Automated translation to GO terms of SwissProt keywords that describe PPARδ indicates that, normally, it is located in the nucleus, has receptor activity and zinc ion binding activity, and is putatively involved in the regulation of transcription, in a DNA-dependent fashion. Previous work further indicates that heart failure is associated with a shift from fatty acid metabolism towards more prominent glucose oxidation to generate ATP. Given the involvement of the PPAR steroid receptor family in activating genes involved in fatty acid oxidation, it has been postulated that PPAR activity is decreased in heart failure, but the precise mechanisms responsible for the down-regulation of PPAR expression and/or activity and down-regulation of fatty acid oxidation in heart failure has remained unclear until the present invention. It was also unknown until the present invention, whether down-regulation of PPARδ is a cause or a result of heart failure.

The present invention now provides the insight that an increase of PPARδ is able to increase or restore fatty acid oxidation, improve energy metabolism, and prevent, diminish or delay heart failure. Increase of PPARδ expression can be achieved either directly or indirectly. According to the present invention, PPARδ is preferably increased by inhibiting miR-199a and/or miR-214.

Now that the invention has provided the insight that inhibition of PPARδ leads to an adverse energy metabolism switch in heart muscle cells and that increasing the expression, amount and/or activity of PPARδ and/or inhibition of a microRNA capable of inhibiting PPARδ is able to improve energy metabolism of heart muscle cells, in a first embodiment, the invention provides a method for treating, diminishing, counteracting, delaying and/or preventing heart disease, comprising administering to an individual in need thereof a pharmaceutically effective amount of an inhibitor of a microRNA, wherein the microRNA is capable of inhibiting or decreasing the expression of PPARδ. Hence, an inhibitor of a microRNA, the microRNA being capable of inhibiting or decreasing the expression of PPARδ, is particularly suitable for use as a medicament. Further provided is, therefore, an inhibitor of microRNA for use in treating, diminishing, delaying and/or preventing heart disease, wherein the microRNA is capable of inhibiting or decreasing the expression of PPARδ.

A use of such inhibitor for the preparation of a medicament is also provided. One embodiment thus provides a use of an inhibitor of microRNA, wherein the microRNA is capable of inhibiting or decreasing the expression of PPARδ for the manufacture of a medicament for treating, diminishing, delaying and/or preventing heart disease.

As used herein, a microRNA capable of inhibiting or decreasing the expression of PPARδ is also referred to as an "anti-PPARδ microRNA."

As used herein, the term "inhibitor of microRNA" comprises compounds that are capable of inhibiting, or at least partly inhibiting, the expression, the amount and/or the activity of microRNA. In case that expression of microRNA causes, aggravates and/or sustains a disease condition, inhibiting or partly inhibiting expression of the microRNA will at least in part counteract, diminish, delay or prevent the disease condition. If expression of a microRNA in an individual is increased as compared to a normal, healthy situation, expression of the microRNA is preferably restored to a normal value, preferably the expression level present in the individual before such increase took place.

Inhibition of microRNA is achieved through several methods. For instance, a nucleic acid molecule that is complementary to at least a functional part of the microRNA is used. The functional part comprises at least 15 nucleotides, preferably at least 18 nucleotides, more preferably at least 20 nucleotides. After administration to a cell, said nucleic acid molecule then binds to the microRNA, thereby counteracting, delaying and/or at least in part inhibiting binding of the microRNA to the target gene and thereby counteracting the function of said microRNA, i.e., gene regulation. A person skilled in the art is aware of various methods to inhibit or partly inhibit microRNA. Non-limiting examples are, for instance, the use of a locked nucleic acid oligo (LNA), in which an extra bridge connecting the 2' and 4' carbons is present, where the bridge "locks" the ribose in the 3'-endo structural conformation. Further, non-limiting examples comprise a Morpholino oligo, a modified antisense molecule that does not degrade its target RNA molecule, and a 2'-O-methyl RNA oligo.

Therefore, in a preferred embodiment, an inhibitor, a use and/or a method according to the invention are provided, wherein the inhibitor comprises a nucleic acid sequence with a length of at least 15 nucleotides, preferably at least 18 nucleotides, more preferably at least 20 nucleotides, that is complementary to the microRNA.

As used herein, a nucleic acid molecule or nucleic acid sequence of the invention preferably comprises a chain of nucleotides, more preferably DNA and/or RNA. More preferably, a nucleic acid molecule or nucleic acid sequence of the invention comprises double-stranded RNA in order to use RNA interference to degrade target RNA. In other embodiments, a nucleic acid molecule or nucleic acid sequence of the invention comprises other kinds of nucleic acid structures such as, for instance, a DNA/RNA helix, peptide nucleic acid (PNA), locked nucleic acid (LNA), Morpholino, 2'-O-methyl RNA oligo and/or a ribozyme. Hence, the term "nucleic acid sequence" also encompasses a chain comprising non-natural nucleotides, modified nucleotides and/or non-nucleotide building blocks that exhibit the same function as natural nucleotides.

Another method for inhibiting microRNA comprises, for instance, interference with the expression of microRNA. The DNA locus that specifies a microRNA is longer than the microRNA, and this DNA region includes both the microRNA sequence plus an approximate reverse complement sequence. (A reverse complement is a region with complementary bases in the reverse order, going from 5'->3' on the same DNA strand.) When this DNA locus is transcribed into a single-stranded RNA (ssRNA) molecule, the microRNA sequence and its reverse-complement base pair to form a double-stranded RNA hairpin loop. This forms a primary microRNA structure (pri-microRNA), which is the first stage in a series of events that occur in cells by which microRNAs affect cell functions. In animals, the nuclear enzyme Drosha cleaves the base of the hairpin in pri-microRNA to form pre-microRNA. The pre-microRNA molecule is then actively transported out of the nucleus into the cytoplasm by Exportin 5, a carrier protein. The Dicer enzyme then cuts 20-25 nucleotides from the base of the hairpin to release the mature microRNA. An example of an inhibitor that interferes with expression of microRNA is the protein Lin28, which inhibits maturation of pre-microRNA into mature microRNA.

In another preferred embodiment, therefore, an inhibitor, a use and/or a method according to the invention are provided wherein the inhibitor comprises a compound, preferably a protein or a nucleic acid molecule, wherein the compound inhibits maturation of pre-microRNA into mature microRNA. In a more preferred embodiment, the compound inhibits maturation by binding to the pre-microRNA.

The genes encoding miRNAs are much longer than the processed mature miRNA molecule; miRNAs are first transcribed as primary transcripts or pri-miRNA with a cap and poly-A tail and processed to short, 70-nucleotide stem-loop structures known as pre-miRNA in the cell nucleus. These pre-miRNAs are then processed to mature miRNAs in the cytoplasm by interaction with the endonuclease Dicer, which also initiates the formation of the RNA-induced silencing complex (RISC).[7] This complex is responsible for the gene silencing observed due to miRNA expression and RNA interference. An inhibitor of microRNA according to the invention also encompasses an inhibitor of pri-miRNA, pre-miRNA or RISC. Another example of interference with expression of microRNA is thus, for instance, by interfering with pri-microRNA translation, for instance, by interfering with the translation of pri-microRNA from DNA. This is, for instance, achieved by providing a compound, preferably a protein or a nucleic acid, that binds to a promoter functionally associated with pri-microRNA, thereby inhibiting expression of pri-microRNA. In another preferred embodiment, therefore, an inhibitor, a use and/or a method according to the invention are provided wherein the inhibitor comprises a compound, preferably a protein or a nucleic acid molecule, wherein the compound binds to a promoter functionally associated with a pri-microRNA, thereby inhibiting expression of pri-microRNA.

There are several hundreds of distinct microRNA molecules and their precursors are clustered together based on their relative distance in the genome: in general, precursors are placed in the same cluster if they are 50 kb or less from each other away. As the invention provides the insight that PPARδ is a direct target of miR-199a and/or 214, in a preferred embodiment, the invention provides an inhibitor of microRNA for use in treating, diminishing, delaying and/or preventing heart disease, wherein the inhibitor is capable of counteracting expression, amount and/or activity of microRNA miR-199a and/or miR-214. An inhibitor, use and/or method according to the present invention, wherein the inhibitor is capable of counteracting expression, amount and/or activity of microRNA miR-199a and/or miR-214, is, therefore, also provided.

An inhibitor of microRNA is especially useful if an efficient amount is able to reach a microRNA that it is supposed to inhibit. Since microRNA is typically present inside a cell, the inhibitor is preferably able to inhibit the microRNA inside the cell. As an inhibitor of an anti-PPARδ microRNA is especially useful for the treatment or prevention of heart disease, the inhibitor is even more preferably able to inhibit expression, amount and/or activity of the anti-PPARδ microRNA within a heart muscle cell. In one embodiment, the inhibitor is capable of being introduced into the cell, preferably a heart muscle cell. In one embodiment, the inhibitor of anti-PPARδ microRNA is itself able to penetrate a cell membrane and enter a cell, preferably a heart muscle cell. However, it is also possible to modify the inhibitor, such that it is thereafter capable of entering a cell, preferably a heart muscle cell. This is, however, not necessary because many transport systems capable of introducing a compound into a cell are known.

Thus, in a preferred embodiment, an inhibitor, a use and/or a method according to the invention is provided, wherein the inhibitor is capable of counteracting, inhibiting and/or decreasing the expression, amount and/or activity of the microRNA, preferably miR-199a and/or miR-214, in a cell, more preferably in a heart muscle cell. A heart muscle cell, also called a cardiac muscle cell or a cardiomyocyte, is a cell similar to, originating from, or derived of a muscle cell, which in a natural situation, is present in the heart of a vertebrate organism. The cell need not to be directly obtained from heart tissue since it is also possible to culture and/or store this kind of cell in vitro.

Methods for introducing an inhibitor of microRNA into a cell are known in the art. Methods for introducing inhibitors, preferably antisense nucleic acid, comprise, for instance, calcium phosphate transfection, DEAE-Dextran, electroporation or liposome-mediated transfection. Alternatively, direct injection of the inhibitor is employed. Preferably, however, a nucleic acid, which is an inhibitor and/or which encodes an inhibitor, is introduced into a cell by a vector, preferably a viral vector. Various terms are known in the art that refer to introduction of a nucleic acid into a cell by a vector. Examples of such terms are "transduction," "transfection" and "transformation." Techniques for generating a vector with a nucleic acid sequence and for introducing the vector into a cell are known in the art. Marker genes such as, for instance, antibiotic resistance or sensitivity genes and/or genes encoding markers, such as cell surface antigens or fluorescent proteins like green fluorescence protein, are preferably used in identifying cells containing the introduced nucleic acid, as is well known in the art.

Preferably, an inhibitor according to the invention is provided that is able to be introduced into a mammalian cell in vivo. Non-limiting examples of methods according to the invention are the coupling of the inhibitor to cell-penetrating peptides, or the use of liposomes containing the inhibitor. Preferably, the inhibitor is targeted to heart muscle cells, for instance, by using artificial HDL-like particles bound to the inhibitor, enhancing delivery to the myocardium.

Inhibition of microRNA in a cell, wherein microRNA is capable of inhibiting or decreasing the expression of PPARδ, leads to an increase or restoration of PPARδ expression in the cell. In a preferred embodiment, therefore, an inhibitor, use and/or method according to the invention is provided wherein the inhibitor of microRNA is capable of increasing and/or restoring the expression of PPARδ in a cell. To be able to counteract the function of microRNA in a cell, the inhibitor is preferably able to penetrate the nucleus. It is generally accepted that small nucleic acid molecules, preferably antisense molecules, such as the before-mentioned LNA, Morpholino, or 2'-O-methyl RNA oligos, can freely move between the cytosol and the nucleus. In one embodiment, however, an inhibitor that is not able to freely move between the cytosol and the nucleus is modified so as to target and penetrate the nuclear membrane. Methods to target the nucleus are well known in the art and include, for instance, the use of nuclear targeting vector, such as an adenovirus vector.

In a preferred embodiment, an inhibitor of microRNA, a use and/or a method according to the invention is provided, wherein the inhibitor comprises an antisense nucleic acid molecule. Preferably, an antisense nucleic acid molecule against a microRNA capable of inhibiting or decreasing the expression of PPARδ is used. The antisense molecule preferably comprises at least 15 nucleotides. Even more preferably, the antisense molecule comprises at least 18 nucleotides. Most preferably, the antisense molecule comprises at least 20 nucleotides.

As said before, the invention provides the insight that miR-199a and miR-214 decrease the expression of PPARδ, which is involved with, and/or enhances, heart disease. Therefore, an inhibitor of the invention preferably inhibits miR-199a and/or miR-214. An inhibitor, use and/or method according to the invention wherein microRNA is miR-199a and/or miR-214 is, therefore, also provided. Preferably, the inhibitor of miR-199a and/or miR-214 comprises a nucleic acid sequence able to bind to miR-199a and/or miR-214 under physiological conditions. FIG. 5 comprises a non-limiting example of a sequence that is capable of binding to miR-199a and/or to miR-214. It is commonly thought that to be able to bind and inhibit the function of microRNA, an antisense nucleic acid is allowed to have a few (preferably one or two) mismatches. Thus, for instance, in the case of a sequence as depicted in FIG. 5, at least 19 nucleotides are preferably identical to the complementary sequence of miR-199a and/or miR-214. Moreover, an antisense nucleic acid is allowed to be somewhat shorter than its target sequence. An antisense against miR-199a and/or miR-214 is preferably at least 17 nucleotides long. In a preferred embodiment, therefore, an inhibitor, use and/or method according to the invention is provided wherein the inhibitor comprises a nucleic acid molecule comprising a sequence with a length of at least 17, preferably at least 19 nucleotides with at least 90% sequence identity to at least 17, preferably at least 19 nucleotides of miR-199a and/or miR-214, or the complement thereof. In one embodiment, the nucleic acid molecule comprises a sequence with a length of at least 19 nucleotides with at least 90% sequence identity to at least part of a sequence shown in FIG. 5, that part having at least 19 nucleotides.

One particularly preferred embodiment provides an inhibitor, a use, and/or a method according to the invention, wherein the inhibitor comprises:
 a nucleic acid sequence with a length of at least 19 nucleotides with at least 90% sequence identity to at least part of the sequence CCCAGUGUUCAGACUACCUG-UUC (SEQ ID NO:1) (hsa-miR-199a-5p) or the complement thereof, the part having at least 19 nucleotides,
 a nucleic acid sequence with a length of at least 19 nucleotides with at least 90% sequence identity to at least part of the sequence ACAGUAGUCUGCACAUUGGUUA (SEQ ID NO:2) (hsa-miR-199a-3p) or the complement thereof, the part having at least 19 nucleotides,
 a nucleic acid sequence with a length of at least 19 nucleotides with at least 90% sequence identity to at least part of the sequence ACAGCAGGCACAGACAGGCAGU (SEQ ID NO:3) (hsa-miR-214) or the complement thereof, the part having at least 19 nucleotides, and/or a nucleic acid sequence with a length of at least 19 nucleotides with at least 90% sequence identity to at least part of the sequence UGCCUGUCUACACUUGCUGUGC (SEQ ID NO:4) (hsa-miR-214*) or the complement thereof, the part having at least 19 nucleotides.

Such nucleic acid sequence with a length of at least 19 nucleotides is particularly suitable for counteracting miR-199a, thereby increasing and/or restoring PPARδ expression in a cell. Hence, as a result, such nucleic acid sequence is particularly suitable for counteracting heart disease and for the preparation of a medicament for counteracting and/or preventing heart disease.

The term "% sequence identity" is defined herein as the percentage of nucleotides in a nucleic acid sequence that is identical with the nucleotides in a nucleic acid sequence of interest, after aligning the sequences and optionally introducing gaps, if necessary, to achieve the maximum percent sequence identity. Methods and computer programs for alignments are well known in the art. As used herein, the terms "nucleic acid sequence" and "nucleotides" also encompass non-natural molecules based on and/or derived from nucleic acid sequences, such as, for instance, artificially modified nucleic acid sequences, peptide nucleic acids, as well as nucleic acid sequences comprising at least one modified nucleotide and/or non-natural nucleotide such as, for instance, inosine, LNA, Morpholino, and 2'-O-methyl RNA.

An inhibitor as described above is thus especially suitable for the manufacture of a medicament for treating, diminishing, delaying and/or preventing heart disease, preferably heart failure. In one embodiment, the invention, therefore, provides a use of an inhibitor of microRNA, wherein microRNA is capable of inhibiting or decreasing the expression of PPARδ for the manufacture of a medicament for treating, diminishing, delaying and/or preventing heart disease, preferably heart failure. In a preferred embodiment, a use according to the invention is provided, wherein the inhibitor comprises a nucleic acid molecule that is complementary to at least 15 nucleotides, preferably at least 18 nucleotides, most preferably at least 20 nucleotides of the microRNA. Further provided is a use according to the invention, wherein the inhibitor is capable of counteracting expression, amount and/or activity of microRNA miR-199a and/or miR-214. In a preferred embodiment, the inhibitor is capable of inhibiting or decreasing the expression of microRNA in a cell, preferably thereby increasing or restoring the expression of PPARδ in the cell. The cell preferably is a heart muscle cell. In yet another preferred embodiment, a use according to the invention is provided, wherein the inhibitor comprises an antisense nucleic acid molecule with a length of at least 19 nucleotides, preferably with at least 90% sequence identity to a sequence shown in FIG. 5, Panel a or the complement thereof. Particularly preferred antisense nucleic acid sequences are sequences with a length of at least 19 nucleotides with at least 90% sequence identity to at least part of the sequence CCCAGUGUUCAGACUACCUGUUC (SEQ ID NO:1) (hsa-miR-199a-5p) or ACAGUAGUCUGCACAUGG-UUA (SEQ ID NO:2) (hsa-miR-199a-3p), or the complement of any of these sequences, the part having at least 19 nucleotides. In one preferred embodiment, the invention, therefore, provides a use of a nucleic acid sequence with a length of at least 19 nucleotides with at least 90% sequence identity to at least part of the sequence CCCAGUGUUCAGACUACCU-GUUC (SEQ ID NO:1) (hsa-miR-199a-5p) or the complement thereof, the part having at least 19 nucleotides, for the manufacture of a medicament for treating, diminishing, delaying and/or preventing heart disease, preferably heart failure. Another preferred embodiment provides a use of a nucleic acid sequence with a length of at least 19 nucleotides with at least 90% sequence identity to at least a part of the sequence ACAGUAGUCUGCACAUGGUUA (SEQ ID NO:2) (hsa-miR-199a-3p) or the complement thereof, the part having at least 19 nucleotides, for the manufacture of a medicament for treating, diminishing, delaying and/or preventing heart disease, preferably heart failure.

In yet another preferred embodiment, a use according to the invention is provided, wherein the inhibitor comprises an antisense nucleic acid molecule with a length of at least 19 nucleotides, preferably with at least 90% sequence identity to a sequence shown in FIG. 5, Panel b or the complement thereof. Particularly preferred antisense nucleic acid sequences are sequences with a length of at least 19 nucleotides with at least 90% sequence identity to at least part of the sequence ACAGCAGGCACAGACAGGCAGU (SEQ ID NO:3) (hsa-miR-214) or UGCCUGUCUACACUUGCU-GUGC (SEQ ID NO:4) (hsa-miR-214*), or the complement of any of these sequences, the part having at least 19 nucleotides. In one preferred embodiment, the invention, therefore, provides a use of a nucleic acid sequence with a length of at least 19 nucleotides with at least 90% sequence identity to at least part of the sequence ACAGCAGGCACAGACAG-GCAGU (SEQ ID NO:3) (hsa-miR-214) or the complement thereof, the part having at least 19 nucleotides, for the manufacture of a medicament for treating, diminishing, delaying and/or preventing heart disease, preferably heart failure. Another preferred embodiment provides a use of a nucleic acid sequence with a length of at least 19 nucleotides with at least 90% sequence identity to at least a part of the sequence UGCCUGUCUACACUUGCUGUGC (SEQ ID NO:4) (hsa-miR-214*) or the complement thereof, the part having at least 19 nucleotides, for the manufacture of a medicament for treating, diminishing, delaying and/or preventing heart disease, preferably heart failure.

With a use according to the invention, it is thus possible to treat, diminish, delay or at least partly prevent a heart disease.

In one embodiment, the invention provides a method for treating, diminishing, counteracting, delaying and/or preventing a heart disease, comprising administering to an individual in need thereof a pharmaceutically effective amount of an inhibitor of microRNA, wherein microRNA is capable of inhibiting or decreasing the expression of PPARδ. In one embodiment, the individual is diagnosed with a heart disease before treatment. A method comprising determining whether a subject is suffering from heart disease and, if the subject appears to be suffering from heart disease, treating the person with a method according to the present invention, is, therefore, also provided. Whether a subject is suffering from heart disease can be determined by any method known in the art. Non-limiting examples of such methods for diagnosing heart disease include cardiac catheterization and angiography, echocardiogram, transesophageal echocardiography (TEE), electrocardiogram (ECG or EKG), use of a Holter monitor and event recorder, MUGA scan, stress testing, thallium and sestamibi (cardiolyte) scans, cardiac MRI and noninvasive screening for coronary artery disease (e.g., CT scan).

Preferably, a method according to the invention is provided, wherein the inhibitor comprises a nucleic acid sequence with a length of at least 15, preferably at least 17, most preferably at least 19 nucleotides that is at least 90% complementary to microRNA, which nucleic acid sequence is preferably capable of counteracting expression, amount and/or activity of microRNA miR-199a and/or miR-214. The nucleic acid sequence is preferably at least 90% complementary to miR-199a and/or miR-214. Even more preferred, a method according to the invention is provided in which the inhibitor is capable of inhibiting or decreasing the expression of microRNA in a cell, even more preferably in a heart muscle cell. In yet another preferred embodiment, a method according to the invention is provided, wherein the inhibitor comprises an antisense nucleic acid molecule, preferably with a length of at least 19 nucleotides with at least 90% sequence identity to a sequence shown in FIG. 5 or the complement thereof.

In another embodiment, a method for counteracting expression of microRNA is provided, wherein an inhibitor according to the invention is expressed in a target cell. In one embodiment, a vector is used that comprises a nucleic acid sequence comprising and/or encoding the inhibitor according to the invention.

The invention thus also provides a vector comprising a nucleic acid sequence, which sequence comprises or encodes an inhibitor of microRNA expression, wherein microRNA is capable of inhibiting or decreasing the expression of PPARδ. The vector preferably comprises a retroviral, adenoviral, adeno-associated viral, or lentiviral vector.

As already described above, it is preferred to increase the expression, amount and/or activity of PPARδ in order to counteract, delay or at least partly prevent heart disease. This can be achieved either indirect, for instance, by decreasing the expression, amount and/or activity of miR-199a and/or miR-214, or direct, through increasing the expression, amount and/or activity of PPARδ. Expression, amount and/or activity of miR-199a and/or miR-214 are preferably counteracted by a nucleic acid sequence that is at least 90% complementary to at least 17, preferably at least 19 nucleotides of miR-199a and/or miR-214. Further provided is, therefore, a vector according to the invention, comprising a nucleic acid molecule with a length of at least 17 nucleotides that is at least 90% complementary to at least 17 nucleotides of microRNA miR-199a and/or miR-214. The vector preferably comprises:
 a nucleic acid sequence with a length of at least 19 nucleotides with at least 90% sequence identity to at least a part of the sequence CCCAGUGUUCAGACUACCU-GUUC (SEQ ID NO:1) (hsa-miR-199a-5p) or the complement thereof, the part having at least 19 nucleotides,
 a nucleic acid sequence with a length of at least 19 nucleotides with at least 90% sequence identity to at least a part of the sequence ACAGUAGUCUGCACAUUGG-UUA (SEQ ID NO:2) (hsa-miR-199a-3p) or the complement thereof, the part having at least 19 nucleotides,
 a nucleic acid sequence with a length of at least 19 nucleotides with at least 90% sequence identity to at least a part of the sequence ACAGCAGGCACAGACAG-GCAGU (SEQ ID NO:3) (hsa-miR-214) or the complement thereof, the part having at least 19 nucleotides, and/or a nucleic acid sequence with a length of at least 19 nucleotides with at least 90% sequence identity to at least a part of the sequence UGCCUGUCUACACU-UGCUGUGC (SEQ ID NO:4) (hsa-miR-214*) or the complement thereof, the part having at least 19 nucleotides.

As said before, it is also possible to increase the expression, amount and/or activity of PPARδ directly. This can, for instance, be achieved through the use of a vector comprising or encoding PPARδ or a PPARδ increasing compound.

One embodiment provides a vector according to the invention comprising a promoter suitable for expression in a mammalian cell. In one embodiment, the promoter is operably linked to a nucleic acid molecule capable of increasing the expression, amount and/or activity of PPARδ. In another embodiment, the promoter is operably linked to a nucleic acid molecule capable of counteracting expression, amount and/or activity of miR-199a and/or miR-214 microRNA. In a particularly preferred embodiment, a vector according to the invention is suitable for expression in a heart muscle cell. In that case, the vector preferably comprises a promoter suitable for expression in a heart muscle cell. In one embodiment, a vector according to the invention comprises a ubiquitous promoter or an organ-specific promoter, preferably a heart muscle cell-specific promoter. Such a vector is especially useful for treating, diminishing, delaying and/or preventing heart disease. In one embodiment, therefore, the invention provides a use of a vector according to the invention for the preparation of a medicament for treating, diminishing, delaying and/or preventing heart disease.

The invention also provides an isolated and/or non-human cell comprising a vector and/or an inhibitor according to the invention. The cell preferably comprises a mammalian cell. In one particularly preferred embodiment, the cell comprises a heart muscle cell. In one embodiment, the cell is part of a non-human test animal. In another embodiment, however, an isolated cell is provided. An isolated cell comprising a vector and/or an inhibitor according to the invention is especially useful for treating, diminishing, delaying and/or at least in part preventing heart disease. In one embodiment, therefore, an isolated cell comprising a vector and/or an inhibitor according to the invention for the use in treating, diminishing, delaying and/or preventing heart disease is provided.

Preferably, the isolated cell comprises a heart muscle cell, a heart muscle progenitor cell or a stem cell. In one embodiment, such heart muscle, progenitor or stem cell is injected into a heart muscle, preferably into a damaged part of a heart, where the cell is capable of expanding and repairing the damaged part. In another embodiment, a cell according to the invention is injected into the circulation of an individual, allowing the cell to engraft into the heart of the individual, preferably into a damaged part of the heart, and (at least partly) repair the damaged part.

In a preferred embodiment, an isolated cell according to the invention is provided, wherein a nucleic acid sequence comprising or encoding an inhibitor according to the invention is present. The nucleic acid sequence is preferably operably linked to a(n exogenous) regulatory element that is specific for myocardial cells. The (exogenous) regulatory element is, for instance, operably linked to an antisense nucleic acid of miR-199a and or miR-214, which antisense nucleic acid is preferably at least 90% identical to at least 17 nucleotides, preferably at least 19 nucleotides of miR-199a and/or miR-214, in order to enhance expression of the antisense nucleic acid in myocardial cells. A use of an exogenous regulatory element that is specific for myocardial cells provides various advantages. For instance, after transduction of stem cells and/or progenitor cells, an inhibitor according to the invention will not be expressed in all kinds of differentiated cells, but mainly in myocardial cells, such that the inhibitor exerts its inhibitory function mainly in myocardial cells, thereby reducing possible side effects in other cell types. An isolated cell according to the invention comprising a vector and/or an inhibitor is also especially useful for the preparation of a medicament, preferably for treating, diminishing, delaying and/or preventing heart disease. The invention thus also provides a use of an isolated cell comprising a vector and/or an inhibitor according to the invention for the preparation of a medicament, preferably for treating, diminishing, delaying and/or preventing heart disease.

Furthermore, a method is provided for treating, diminishing, delaying and/or preventing a heart disease, comprising administering to an individual in need thereof a pharmaceutically effective amount of a vector and/or a cell according to the invention. The invention further provides a pharmaceutical composition comprising an inhibitor of microRNA, wherein microRNA is capable of inhibiting or decreasing the expression of PPARδ, the pharmaceutical composition further comprising a pharmaceutically acceptable carrier, diluent or excipient. The inhibitor preferably comprises a miR-199a and/or miR-214 inhibitor, preferably a nucleic acid sequence with a length of at least 17, preferably at least 19 nucleotides, which is at least 90% identical to at least 17, preferably at least 19 nucleotides of miR-199a and/or miR-214, or the complement thereof. A pharmaceutical composition comprising a vector and/or an isolated cell according to the invention, further comprising a pharmaceutically acceptable carrier, diluent or excipient, is also provided. Suitable carriers, diluents, excipients and the like are commonly known in the art of pharmaceutical formulation and may be readily found and applied by the skilled artisan, references, for instance, *Remington's Pharmaceutical Sciences*, Mace Publishing Company, Philadelphia Pa., 17th ed. 1985.

A pharmaceutical composition according to the invention is presented in any form, for example, as a tablet, as an injectable fluid or as an infusion fluid, etc. Moreover, the inhibitor, vector and/or cell according to the invention can be administered via different routes, for example, intravenously, bronchially, or orally. Yet another suitable route of administration is local injection, preferably into the heart muscle.

In a preferred embodiment, the used route of administration is intravenously. It is clear for the skilled person that preferably a therapeutically effective amount of an inhibitor, vector and/or cell according to the invention is delivered. Dose ranges of inhibitors, vectors, cells and/or other molecules according to the invention to be used in the therapeutic applications as described herein are designed on the basis of rising dose studies in the clinic in clinical trials for which rigorous protocol requirements exist. As a starting point, a dose of between 0.01 and 100 mg/kg/day is used.

The present invention provides the insight that inhibition of PPARδ leads to heart disease that can be counteracted, diminished, delayed and/or prevented by increasing the expression, amount and/or activity of PPARδ and/or inhibition of a microRNA capable of inhibiting PPARδ. The invention, therefore, further provides a use, a method, a vector, an inhibitor, a cell, and/or a pharmaceutical composition according to the invention, wherein heart disease is associated with microRNA expression and/or decreased or inhibited expression of PPARδ. Preferably, the microRNA is miR-199a and/or miR-214.

Decreasing the expression, amount and/or activity of miR-199a and/or miR-214, and/or increasing the expression, amount and/or activity of PPARδ is particularly useful for counteracting, diminishing, delaying or at least in part preventing hypertrophic heart disease and/or heart failure and/or a heart disease that is related to a condition after heart-ischemia, diabetes, hypertension, and/or at least one inherited genetic mutation that causes any form of early- or late-onset congenital heart disease.

Further provided is, therefore, a use, a method, a vector, an inhibitor, a cell, and/or a pharmaceutical composition according to the invention, wherein the heart disease is hypertrophic heart disease, preferably heart failure. In a preferred embodiment, the heart disease is associated with a condition after heart-ischemia, diabetes, and/or hypertension, and/or related condition associated with at least one inherited genetic mutation that causes early- or late-onset congenital heart disease. In a preferred embodiment, the invention provides a method for counteracting, diminishing, treating, delaying or preventing a heart disease associated with a condition after heart-ischemia, diabetes, and/or hypertension, and/or associated with at least one inherited genetic mutation that causes a form of early- or late-onset congenital heart disease, comprising administering to a subject in need thereof a pharmaceutically effective amount of a vector, an inhibitor, an isolated cell, and/or a pharmaceutical composition according to the invention, preferably after the subject has been diagnosed with that heart disease.

In yet another embodiment, the invention provides a non-human test animal that has been provided with an inhibitor of microRNA, wherein microRNA is capable of inhibiting or decreasing the expression of PPARδ. The inhibitor preferably comprises a miR-199a and/or miR-214 inhibitor. A non-human test animal that has been provided with a vector, an isolated cell, and/or a pharmaceutical composition according to the invention is also provided. Such a non-human test animal is especially useful for screening, detection and/or identification of candidate compounds capable of inhibiting or decreasing expression, amount and/or activity of miR-199a and/or miR-214. Such non-human test animal is also especially useful for screening, detection and/or identification of candidate compounds capable of increasing and/or restoring the expression, amount and/or activity of PPARδ. Hence, a non-human test animal according to the invention is especially useful for screening, detection and/or identification of candidate compounds capable of counteracting, diminishing, delaying or preventing heart disease.

Screening methods for candidate compounds are especially useful for identifying new inhibitors and are, therefore, also herewith provided. A screening method, for instance, comprises contacting a candidate compound with an isolated cell or a non-human animal and measuring the expression, amount and/or activity of miR-199a and/or miR-214 and/or PPARδ. The expression, amount and/or activity of miR-199a and/or miR-214 and/or PPARδ is preferably compared with the expression, amount and/or activity of miR-199a and/or miR-214 and/or PPARδ in the same kind of cell or animal without the candidate compound. A decreased miR-199a and/or miR-214 and/or an increased PPARδ expression, amount and/or activity in the cell or animal with the candidate compound relative to the cell or animal without the candidate compound, indicates that the candidate compound is able to counteract and/or prevent heart disease. Further provided is, thus, a method for determining whether a candidate compound is able to counteract and/or prevent heart disease, comprising contacting the candidate compound with an isolated cell and/or a non-human test animal and measuring expression, amount and/or activity of miR-199a and/or miR-214 and/or PPARδ in the cell and/or the animal, further comprising comparing the measured expression, amount and or activity with the expression, amount and or activity of miR-199a and/or miR-214 and/or PPARδ in the same kind of cell or animal without the candidate compound, wherein decreased miR-199a and/or miR-214 and/or increased PPARδ expression, amount and/or activity in the cell or animal with the candidate compound relative to the cell or animal without the candidate compound, indicates that the candidate compound is able to counteract and/or prevent heart disease. Preferably, the candidate compound is contacted with a cell that shows increased miR-199a and/or miR-214 and/or decreased PPARδ expression, amount and/or activity as compared to a healthy cell or animal. The increase in miR-199a and/or miR-214 expression, amount or activity and/or decrease in PPARδ expression, amount and/or activity preferably results in hypertrophy in the cell. Contacting the hypertrophic cell with a candidate compound and measuring the expression, amount and/or activity of miR-199a and/or miR-214 and/or PPARδ and/or measuring the shape and size of the cell, and comparing the measurements with reference values, for instance, of the cell before contacting the cell with candidate compound or, for instance, an isolated and/or non-human cell that is not contacted with the candidate compound, identifies compounds that are able to inhibit miR-199a and/or miR-214, increase PPARδ expression, amount and/or activity, and/or decrease or inhibit hypertrophy of the cell.

One embodiment provides a screening method comprising administering a candidate compound to a non-human test animal and measuring the expression, amount and/or activity of miR-199a and/or miR-214 and/or PPARδ and comparing the measurement(s) with a reference value as described above. Preferably, the non-human test animal exhibits increased miR-199a and/or miR-214 and/or decreased PPARδ expression, amount and/or activity before contacting the animal with the compound. The invention provides the insight that such a non-human test animal is at higher risk of developing heart disease, in particular heart failure. Contacting the animal with an inhibitor according to the invention will counteract, prevent, delay or diminish the heart disease. Such an animal is thus especially useful for screening a candidate compound for its ability of preventing, treating, delaying and/or diminishing heart disease. Additionally, or alternatively, a cell according to the invention is used. In one embodiment, therefore, the invention provides a method for screening a candidate compound, comprising contacting the candidate compound with an isolated cell and/or a non-human test animal and measuring expression, amount and/or activity of miR-199a and/or miR-214 and/or PPARδ in the cell and/or the animal and comparing the measurement with a reference value obtained, for instance, from the cell or the animal before contacting the cell or the animal with the candidate compound or, for instance, from another cell or animal that is not contacted with the candidate compound. The reference cell or reference animal is preferably the same kind of cell, or an animal of the same species, as the test cell or test animal in order to facilitate the comparison. A decrease in miR-199a and/or miR-214 and/or increase in PPARδ expression, amount and/or activity in the test cell or test animal demonstrates that the candidate compound is able to counteract and/or prevent heart disease, in particular heart failure.

In a preferred embodiment, the candidate compound is contacted with an isolated cell or non-human test animal exhibiting increased miR-199a and/or miR-214 or decreased PPARδ expression, amount and/or activity as compared to a normal, healthy cell or animal of the same kind. An isolated and/or non-human cell exhibiting increased miR-199a and/or miR-214 and/or decreased PPARδ expression, amount and/or activity, is especially useful because it changes its shape and size, i.e., the cell becomes hypertrophic. Counteracting the increase of miR-199a and/or miR-214 and/or decrease of PPARδ counteracts the change in energy metabolism, shape and size. Such a cell is thus particularly useful for screening purposes, as the read-out of the screening is easily performed, for instance, with a microscope or through measuring mitochondrial function. A non-human test animal exhibiting increased miR-199a and/or miR-214 and/or decreased PPARδ expression, amount and/or activity is also particularly useful for screening purposes, because such an animal is developing heart disease or is at risk of developing heart disease. A candidate compound capable of counteracting and/or preventing heart disease is thus easily identified in that animal. Further provided is, therefore, an isolated cell or a non-human animal, wherein the expression amount and/or activity of miR199a or miR214 is increased as compared to a natural, healthy cell or animal of the same kind. Further provided is an isolated cell or a non-human animal, wherein the expression amount and/or activity of PPARδ is decreased as compared to a natural, healthy cell or animal of the same kind.

The invention thus provides a screening method comprising contacting a candidate compound with an isolated cell or non-human test animal, preferably showing increased miR-199a and/or miR-214 and/or decreased PPARδ expression, amount and/or activity, further comprising assessing the shape and/or size of the isolated cell and/or the severity and/or risk of heart disease, preferably heart failure, in the non-human test animal and comparing the size and/or shape of the cell, and/or severity and/or risk of the heart disease in the non-human test animal with a reference value. The reference value may be obtained from the same cell or same animal, for instance, before contacting the cell or animal with the candidate compound. The reference value may also be obtained from another cell or animal, preferably of the same kind or species, which, for instance, is not contacted with the candidate compound. A change in value, preferably a decrease in cell size and/or a decrease in risk and/or severity of heart disease indicates whether the candidate compound is able to counteract heart disease.

One preferred embodiment, therefore, provides a method for determining whether a candidate compound is able to counteract and/or prevent heart disease, comprising contacting the candidate compound with an isolated cell and/or a non-human test animal, wherein the isolated cell and/or the non-human test animal preferably shows increased miR-199a and/or miR-214 or decreased PPARδ expression, amount and/or activity, and wherein expression, amount and/or activity of miR-199a, miR-214 and/or PPARδ, the shape and size of the isolated cell, and/or the severity and/or incidence of developing a heart disease, preferably heart failure in the non-human test animal is measured, further comprising comparing the measured expression, amount and/or activity, the shape and/or size, and/or the incidence and/or severity with the corresponding values of the same kind of cell or non-human animal without the candidate compound, wherein decreased miR-199a and/or miR-214 and/or increased PPARδ expression, amount and/or activity, a decrease in size, and/or a decrease in incidence and/or severity of heart disease, relative to the cell or non-human animal without the candidate compound, indicates that the candidate compound is able to counteract and/or prevent heart disease.

Candidate compounds, identified with a method according to the present invention, are especially useful for the treatment of miR-199a- and/or miR-214-related and/or PPARδ-related diseases, for instance through inhibition of miR-199a and/or miR-214, including the treatment of heart disease, preferably heart failure. Such compounds, as well as their use against heart disease and their use for the preparation of a medicament against heart disease, are, therefore, also provided.

The invention provides the insight that heart disease, for instance, heart failure, is related to decreased expression of PPARδ and that miR-199a and/or miR-214 is able to accomplish just this. However, as outlined before, there are hundreds of microRNAs already known, and a number of several thousand different microRNAs has been predicted to exist in mammalians, and each and every one of them is generally thought to regulate hundreds of genes. Thus, next to miR199a and/or miR-214, there are other microRNAs that are capable of regulating expression of PPARδ. Counteracting any of these microRNAs are useful for increasing or restoring the expression of PPARδ. It is also possible to indirectly inhibit or decrease the expression of miR199a and/or miR-214, e.g., through manipulation of transcription factors that regulate miR199a and/or miR-214, thereby indirectly increasing the expression of PPARδ. The current views in the art suggest that miRNA expression is mainly controlled at the transcriptional level.

In one embodiment, therefore, the invention further provides a method for treating, diminishing, delaying or preventing a heart disease, comprising decreasing or inhibiting expression of miR-199a and/or miR214 and/or increasing or restoring the expression, amount and/or activity of PPARδ in a subject suffering from, or at risk of suffering from, heart disease.

It is, of course, also possible to directly influence PPARδ without the use of, for instance, miR-199a and/or miR214. It is, for instance, possible to increase expression, amount and/or activity of endogenous PPARδ or to administer exogenous PPARδ and/or a nucleic acid encoding PPARδ in order to increase the amount and/or (overall) activity of PPARδ.

In yet another embodiment, the invention thus provides a compound capable of increasing or restoring the expression, amount and/or activity of PPARδ for use as a medicament. A compound capable of increasing or restoring the expression, amount and/or activity of PPARδ is preferably used in treating, diminishing, delaying and/or preventing heart disease, or for the preparation of a medicament against heart disease. In one preferred embodiment, the compound comprises a nucleic acid sequence comprising a sequence encoding PPARδ or a functional equivalent thereof.

The invention is further explained in the following examples. These examples do not limit the scope of the invention, but merely serve to clarify the invention.

DETAILED DESCRIPTION OF THE INVENTION

Examples

Materials and Methods

Figure 1:
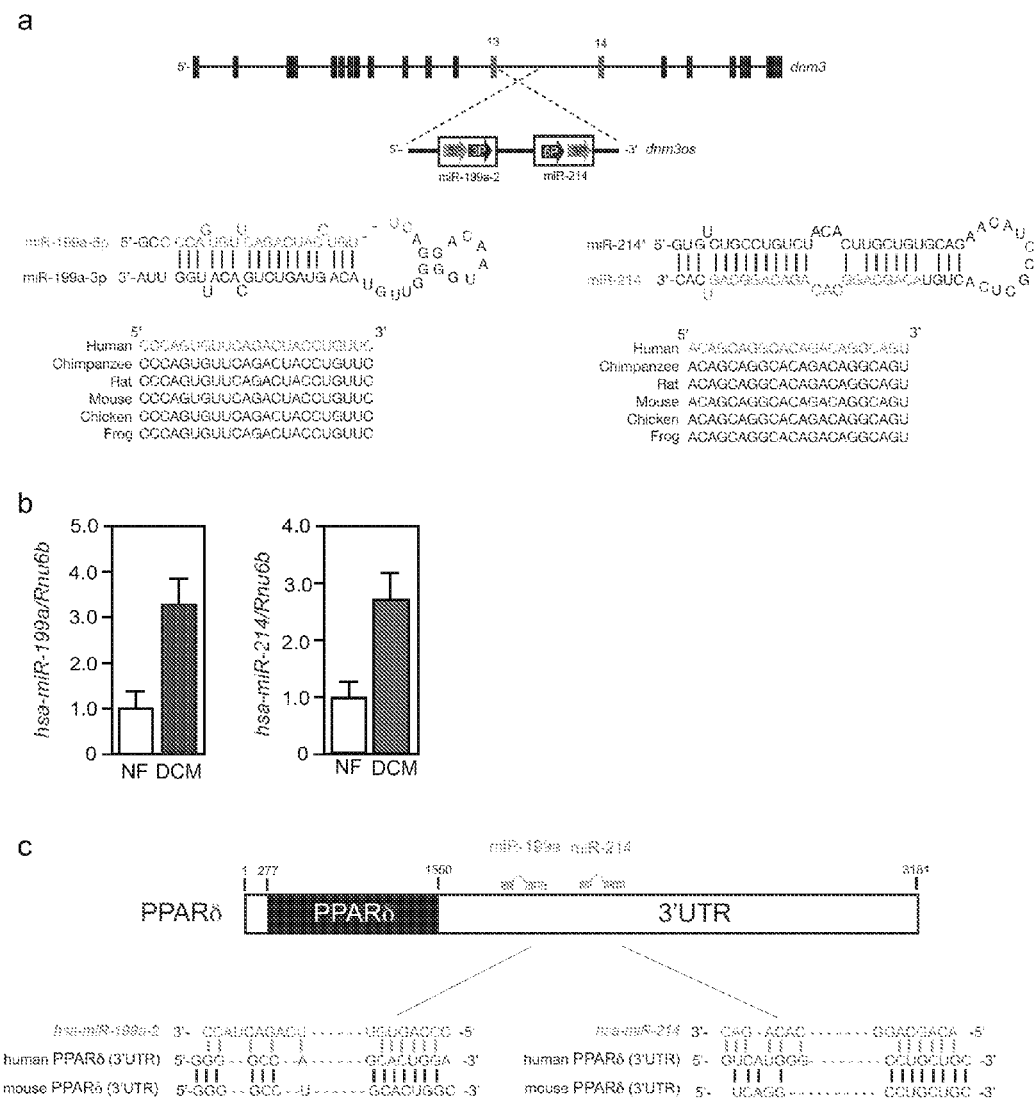
FIG. 1. The miR-199a-2/miR-214 cluster is conserved and associates with down-regulation of PPARδ expression. (A) Depiction of the genomic location of the miR-199a-2/miR214 cluster in an intronic region in the antisense direction of the dynamin 3 (dnm3) gene. The mature microRNAs for miR-199a-2 and miR-214 are fully conserved among many species. Sequences shown include miR-199a-5p (SEQ ID NO:7); miR-199a-3p (SEQ ID NO:8); a hairpin (SEQ ID NO:20) constructed from miR-199a-5p and miR-199a-3p; human miR-199a-5p (SEQ ID NO:1); chimpanzee miR-199a-5p (SEQ ID NO:1); rat miR-199a-5p (SEQ ID NO:1); mouse miR-199a-5p (SEQ ID NO:1); chicken miR-199a-5p (SEQ ID NO:1); frog miR-199a-5p (SEQ ID NO:1); miR-214* (SEQ ID NO:10); miR-214 (SEQ ID NO:9); a hairpin (SEQ ID NO:21) constructed from miR-214* and miR-214; human miR-214 (SEQ ID NO:3); chimpanzee miR-214 (SEQ ID NO:3); rat miR-214 (SEQ ID NO:3); mouse miR-214 (SEQ ID NO:3); chicken miR-214 (SEQ ID NO:3); and frog miR-214 (SEQ ID NO:3). (B) Real time PCR validation of the up-regulation of miR-199a-2 and miR-214 in human failing hearts compared to normal human hearts. (C) Depiction of the microRNA bindings sites and their conservation among species in the 3'UTR region of PPARδ. Sequences shown include hsa-miR-199a-2 5' fragment (5'-CCCAGUGU-3'); hsa-miR-199a-2 3' fragment (SEQ ID NO:11); human PPARδ (3'UTR) (SEQ ID NO:13); mouse PPARδ (3'UTR) (SEQ ID NO:14); hsa-miR-214 5' fragment (5'-ACAGCAGG-3'); hsa-miR-214 3' fragment (5'-CACAGAC-3'); hsa-miR-214 (SEQ ID NO:15); human PPARδ (3'UTR) (SEQ ID NO:16); and mouse PPARδ (3'UTR) (SEQ ID NO:17). (D) HEK293 cells were left untreated, or transfected with precursor for the indicated microRNAs, and Western blots were performed for PPARδ and GAPDH (loading control). (E) Western blot analysis for PPARδ shows down-regulation of endogenous PPARδ in pressure-overloaded mouse hearts (TAC) compared to sham operated control hearts, and down-regulation of PPARδ in human failing hearts compared to control hearts. Western blots were also probed for GAPDH to ensure equal loading. Error bars are mean±SEM of n=3.

Mice.

For aortic banding procedures, we made use of two-month-old wild-type B6CBA. Mice homozygous for PPARδ-floxed alleles (ppard$^{F/F}$) and transgenic αMHC-MerCreMer (αMHC-MCM)[1] mice were crossed to generate double-transgenic (αMHC-MCM-ppard$^{F/F}$) mice. Mice at eight weeks of age (αMHC-MCM-ppard$^{F/F}$ and control ppard$^{F/F}$) were treated with vehicle or tamoxifen (20 mg/kg/day) by daily intraperitoneal injections for five consecutive days. Tamoxifen was diluted in 10/90% v/v ethanol/oil to a concentration of 1 mg/100 µl, for the vehicle group, only ethanol/oil solution was injected. All protocols were performed according to institutional guidelines and were approved by local Animal Care and Use Committees.

Aortic Banding.

Transverse aortic banding (TAC) or sham surgery was performed in two-month-old wild-type B6CBA by subjecting the aorta to a defined, 27 gauge constriction between the first and second truncus of the aortic arch as described previously in detail.[3] Doppler echocardiography was used to calculate the pressure gradient between the proximal and distal sites of the transverse aortic constriction using the Doppler-estimated Bernoulli's equation, and only mice with a pressure gradient>20 mm Hg were included.

Histological Analysis and Immunofluorescence Microscopy.

For histological analysis, hearts were arrested in diastole, perfusion-fixed with 4% paraformaldehyde, embedded in paraffin and sectioned at 5 μm. Paraffin sections were stained with hematoxylin and eosin (H&E) for routine histological analysis; Sirius Red for the detection of fibrillar collagen; FITC-labeled wheat-germ-agglutinin (WGA) to visualize and quantify the cross-sectional area of the cardiomyocytes and CD31 (marker of platelet endothelial cell adhesion molecule-1, PECAM-1) to visualize and quantify the number of capillaries per myofiber. Slides were visualized using a Nikon Eclipse E600 microscope or a Zeiss Axiovert 135 (immunofluorescence). Cell surface areas were determined using SPOT-imaging software (Diagnostic Instruments).

Transthoracic Echocardiography.

echocardiographic measurements were performed on mice anesthetized with isofluorane as described before,[2] one week after starting of tamoxifen treatment.

RNA Isolation from Human Tissue and Mouse Tissue.

We isolated total RNA from human and mouse tissues or from cultured mammalian cells. Mice were sacrificed by cervical dislocation under isofluorane anesthesia. Whole hearts were removed, cleaned in PBS, placed in a labeled tube containing 1 ml of TRIzol reagent (Invitrogen) and immediately put into liquid nitrogen. Tissues were homogenized several times at maximum speed, each time for about 1 minute (to prevent overheating), until complete disruption. Cells cultured in six-well plates to 100% of confluency were washed twice with PBS before adding 1 ml of Trizol per well and collecting the cell lysates in RNase-free tubes. After shaking the homogenates for 10 minutes at 4° C. (to permit the complete dissociation of nucleoprotein complexes), 0.3 ml of chloroform per 1 ml of TRIzol were added to each sample. Centrifugation at 12,000 g for 15 minutes at 4° C. results in the separation of RNA (upper aqueous phase) from DNA and proteins (organic lower and intermediate phase). Aqueous phases (60% of the sample volume) were collected in new RNase-free tubes and RNA was precipitated with 0.5 ml of isopropanol by incubation at −20° C. for at least 1 hour and centrifugation at 12,000 g for 30 minutes at 4° C. The pellets containing the RNA were washed twice with 1 ml of 70% ethanol at 12,000 g for 5 minutes at 4° C. After decantation of the ethanol and total removal by evaporation, samples were dissolved in 20-30 μl of RNase-free water. RNA quantity from the individual tissues was measured with a NANODROP® ND-1000 UV-Vis Spectrophotometer (Wilmington), and RNA quality was monitored using an Agilent 2100 bioanalyzer.

MicroRNA Expression Profiling and Data Analysis.

The expression analysis of 875 mature human miRNA sequences (miRBase V12) was performed by a miRNA-profiling service (LC Sciences Inc., Houston). In short, five μg of total RNA pooled from four control samples (four explanted human control hearts) and seven diseased human heart samples (seven explanted human dilated cardiomyopathy hearts) expression profiling service using μPARAFLO® technology and proprietary probe design, which enable highly sensitive and specific direct detection of miRNAs by single color labeling, hybridization, image data processing and data analysis. The data analysis included multi-array normalization, t-test, ANOVA, False Discovery Rate calculator, and clustering analysis.

Northern blotting. Three micrograms of total RNA from heart or other different tissues were fractionated on a denaturing 12% polyacrylamide gel containing 8 M urea, transferred to Nytran N membrane (Schleicher & Schuell, Germany) by capillary method and fixed by UV cross-linking according to the manufacturer's instructions. Membranes were hybridized with specific 5'-Digoxigenin (Dig)-labeled LNA detection probes (Exiqon) for hsa-miR-199a, hsa-miR-214 or Rnu6-2 (loading control). Detection was performed with an antibody against Dig (Roche).

Primary Neonatal Rat Cardiomyocyte Cultures and miRNA Precursor/Anti-miR Transfections.

Neonatal rat ventricular myocytes were obtained by enzymatic dissociation of one- to two-day-old rat neonatal ventricles as described previously in detail.[5] Ventricles were stored in HEPES buffered DMEM (pH 7.4) prior to multiple rounds of enzymatic digestion in DMEM nutrient mixture F-12 Ham base (Sigma) supplemented with 0.7 mg/ml collagenase type 2 (Invitrogen) and 1 mg/ml pancreatin (Sigma). Cells were collected by centrifugation at 61×g for 10 minutes, resuspended in neonatal calf serum (Invitrogen) and stored in an incubator at 37° C. All cell suspensions were pooled, centrifuged at 61×g for 10 minutes and resuspended in DMEM (Invitrogen) supplemented with 10% horse serum (Invitrogen) and 5% fetal calf serum (Invitrogen). Subsequently, the cells were differentially plated for three hours in uncoated cell culture dishes to remove contaminating non-myocytes. The cardiomyocytes (containing less than 5% non-myocytes) were then plated on fibronectin (Sigma)-coated six-well culture dishes. Approximately 24 hours after plating, the media was replaced by DMEM:M199 (4:1) medium (serum-free medium). For transfection, neonatal rat cardiomyocytes were plated in DMEM supplemented with Nutridoma (Roche) in six-well gelatin-coated plates with density of $2*10^5$ cells per well. The next day, cells were transiently transfected with precursor or anti-miR molecules. miR-199a, miR-214 precursor or anti-miR molecules were obtained from Ambion (Pre-miR™ mmu-miR-199a and/or miR-214miRNA Precursor, pre-miR-199a/214; Anti-miR™ miRNA molecules, anti-miR-199a/214). 30 nM of pre-miR-199a, pre-miR-214, anti-miR-199a, anti-miR-214 or the respective scrambled controls, were transfected with oligofectamine reagent (Invitrogen) according to the manufacturer's recommendations. Cells were washed the next day and left untreated, stimulated with 10 μM phenylephrine (PE) for 24 hours before cell fixation or RNA isolation.

Immunocytochemistry and Confocal Microscopy.

To visualize cardiomyocyte size and sarcomeric organization, cultured cardiomyocytes were fixed for 10 minutes in 4% paraformaldehyde and permeabilized with 0.2% Triton X-100 in PBS for 5 minutes. Primary and secondary antibodies were diluted using 1% BSA in TBS and incubations were carried out at room temperature for 1 hour. Cells were washed three times with PBS for 5 minutes, mounted with coverslips in Vectashield mounting medium for fluorescence (Vector Laboratories), and analyzed by confocal microscopy using a Zeiss LSM 510 META microscope. Antibodies used included mouse monoclonal anti α-actinin (Sigma, 1:500); rabbit polyclonal anti ANF (Peninsula Laboratories) Cy5 goat anti-rabbit and Cy3 goat anti-mouse (Jackson Immuno Research, 1:100 and 1:500, respectively); and TOPRO-3 (1:100, Invitrogen). Cell surface areas were determined using SPOT-imaging software (Diagnostic Instruments) on 80-100 cardiomyocytes in 10 to 20 fields in three independent experiments.

Target Prediction, Primer Designing and Real-Time PCR.

To find the target genes of a specific microRNA, we made use of several web servers based on predictive bioinformatics algorithms (PicTar, miRanda, miRBase). These are intuitive interfaces that incorporate processing algorithms and powerful miRNA target search tools to search the miRNA targets against the most conserved 3' UTR sequences from UCSC Genome Browser. By comparing the target gene lists resulting from each algorithm, we shortened the initial lists of hundreds of potential target genes to a list of ten genes, common to all algorithms used. We designed primers targeted against transcripts of indicated genes and L7. The primers were specific for mouse sequences (www.ensembl.org) and selected using Beacon Designer software (Invitrogen) based on the following requirements: i) primer melting temperature of ~60° C., ii) GC-content of ~55%, iii) preferably no G at 5' end, iv) avoid runs of more than three identical nucleotides, and v) amplicon length of ~100 nucleotides. Specificity was checked with the Basic Local Alignment Search Tool (BLAST) and the specific melting point of the amplicons was analyzed using Biorad Dissociation curve software (iCycler, Biorad). All primer sets were tested for PCR efficiency and alternative primers were designed in case they fell outside the 5% efficiency range ($3.14 \leq slope \leq 3.47$). Three µg of RNA from indicated hearts was reverse-transcribed using Superscript II reverse transcriptase (Invitrogen). PCR amplification was performed (in duplicate) as a singleplex reaction with 400 nM forward and reverse primers on 40 ng cDNA, in a total reaction volume of 25 µl. The PCR was cycled between 95° C./30 seconds and 60° C./30 seconds for 40 cycles, following an initial denaturation step at 95° C. for 3 minutes. Real-time PCR results were verified by electrophoresis of the reverse transcribed material in 1.2% agarose gels and visualized under UV illumination after ethidium bromide staining. Transcript quantities were compared to the amount of endogenous control (L7). Primer sequences are available upon request.

Western Blot Analysis.

Proteins were extracted from cultured cells or heart samples using cell lysis buffer (20 mM Tris pH 8.0, 150 mM NaCl, 1 mM EDTA, 1 mM EGTA, 1% Triton X-100) supplemented with a protease inhibitor cocktail (Complete Mini, Roche). SDS PAGE electrophoresis and blotting was performed as described in detail.[6] Antibodies used included rabbit polyclonal against PPARδ and mouse-monoclonal antibody to GAPDH (both from Santa Cruz), followed by corresponding horseradish peroxidase (HRP)-conjugated secondary antibodies (DAKO) and ECL detection.

Validation of Target Genes.

3' UTR regulatory sequences have been shown to be important for mRNA stability, translation, and transport. We designed primers (5'-AGGCCGCAGCCCAGGCCTCCCC-3' (SEQ ID NO:5) and 5'-CTGGGAATATGGCTCCCG-GCC-3' (SEQ ID NO:6)) specific for mouse sequences targeting the specific binding site of miR-199a and/or miR-214 on the 3'UTR of mouse ppard (nucleotides 1549-2128). We cloned part of mouse ppard 3'UTR that harbored both miR-199a and miR-214 binding sites. After PCR amplification of this specific sequence, a PCR product with the expected size (579 bp) was visualized and isolated from a 1.2 agarose gel. After purification, the 3'UTR fragment was cloned into a pMIR-REPORT™ miRNA expression reporter vector (Ambion). This vector contains firefly luciferase under the control of the CMV mammalian promoter, with a miRNA target cloning region downstream of the luciferase translation sequence. This vector is optimized for cloning of miRNA targets and evaluation of miRNA regulation and, therefore, can be used as a screening tool to identify miRNA targets. After plasmid isolation and sequencing, the plasmid was used to transfect HEK293 cells. Cells were cultured in 96-well plates, transfected with the pmiR-reporter-3'UTR ppard plasmid or the empty vector and incubated for 24 hours at 37° C. After one wash with PBS, cells were left untreated or were treated with indicated precursor or anti-miR molecules or expression vectors for Twist1 and/or HIF-1α for 48 hours before measuring luciferase activity.

Statistical analysis.

The results are presented as mean values±standard error of the mean (SEM). Statistical analyses were performed using Prism 5 software (GraphPad Software Inc.) and consisted of ANOVA followed by Turkey's post-test when group differences were detected at the 5% significance level, or Student's T-test when comparing two experimental groups.

Results

Differential Expression of microRNAs in Human Heart Failure.

We profiled the expression levels of microRNAs in healthy human myocardium versus human dilated cardiomyopathy. RNA was isolated from frozen left ventricular free wall biopsies and we performed microRNA profiling on these samples. We detected microRNAs that are co-regulated with the development of human heart failure and we have analyzed the genomic localization of two specific microRNAs: hsa-miR-199a-2 and hsa-miR-214 (FIG. 1, Panel a; miR-199a-2/miR-214). Both microRNAs are co-expressed in a cluster within an intronic region of the dynamin 3 gene (dnm3), and expressed in one single transcript designated dnmos3 in an antisense manner relative to dnm3 transcription. We validated our microarray expression profiling results using real-time PCR analyses (FIG. 1, Panel b), and could confirm a highly similar induction of both miR-199a-3 and miR-214 in human biopsies of dilated cardiomyopathy compared to healthy human hearts.

Mir-199a-2/miR-214 is Predicted to Target PPARδ.

Despite the large number of identified miRNAs in several disease situations, only a handful of miRNAs have been functionally characterized. Complicated expression patterns and large numbers of predicted target genes preclude a straightforward analysis of their precise biological function. To understand the role of miR-199a-2/miR-214 in human heart failure, we undertook an expression analysis of predicted hsa-miR-199a-2/miR-214 mRNA targets listed in several public datasets developed based on several studies. A consistent target of both microRNAs in this cluster was the delta isoform of peroxisome proliferator activated receptor (PPARδ), expressed from the human gene ppard on chromosome 13. We identified binding sites for both miR-199a and miR-214 in the 3'UTR of PPARδ, and the binding sites were conserved between mouse and human, especially the microRNA seed site (FIG. 1, Panel c), suggesting the functionality of these binding sites.

PPARδ is Down-Regulated by mir-199a-2/miR-214.

To more directly test whether PPARδ is a direct target gene of miR-199a-2/miR-214, we transiently transfected the respective precursor molecules of either miR-199a-2 and miR-214 in HEK293 cells, and performed Western blotting for endogenous PPARδ levels. The data show that both miR-199a and miR-214 expression directly provoked down-regulation PPARδ. The level of down-regulation was similar between miR-199a precursor transfection as for miR-214 precursor, and no additive effect was observed when both precursors were co-transfected (FIG. 1, Panel d). To test whether under conditions of miR-199a/miR-214 up-regulation in vivo, PPARδ expression was also down-regulated, we performed Western blotting on pressure-overloaded mouse hearts and human heart samples from patients with dilated cardiomyopathy. In both situations, PPARδ expression amounted to approximately to half control conditions (FIG. 1, Panel e). Taken together, these data show that miR-199a-2/miR-214 expression inversely correlated with PPARδ expression in cultured cells, pressure-overloaded mouse hearts and in human failing hearts.

PPARδ is a Direct Target Gene of the miR-199a-2/miR-214 Cluster.

Figure 2:
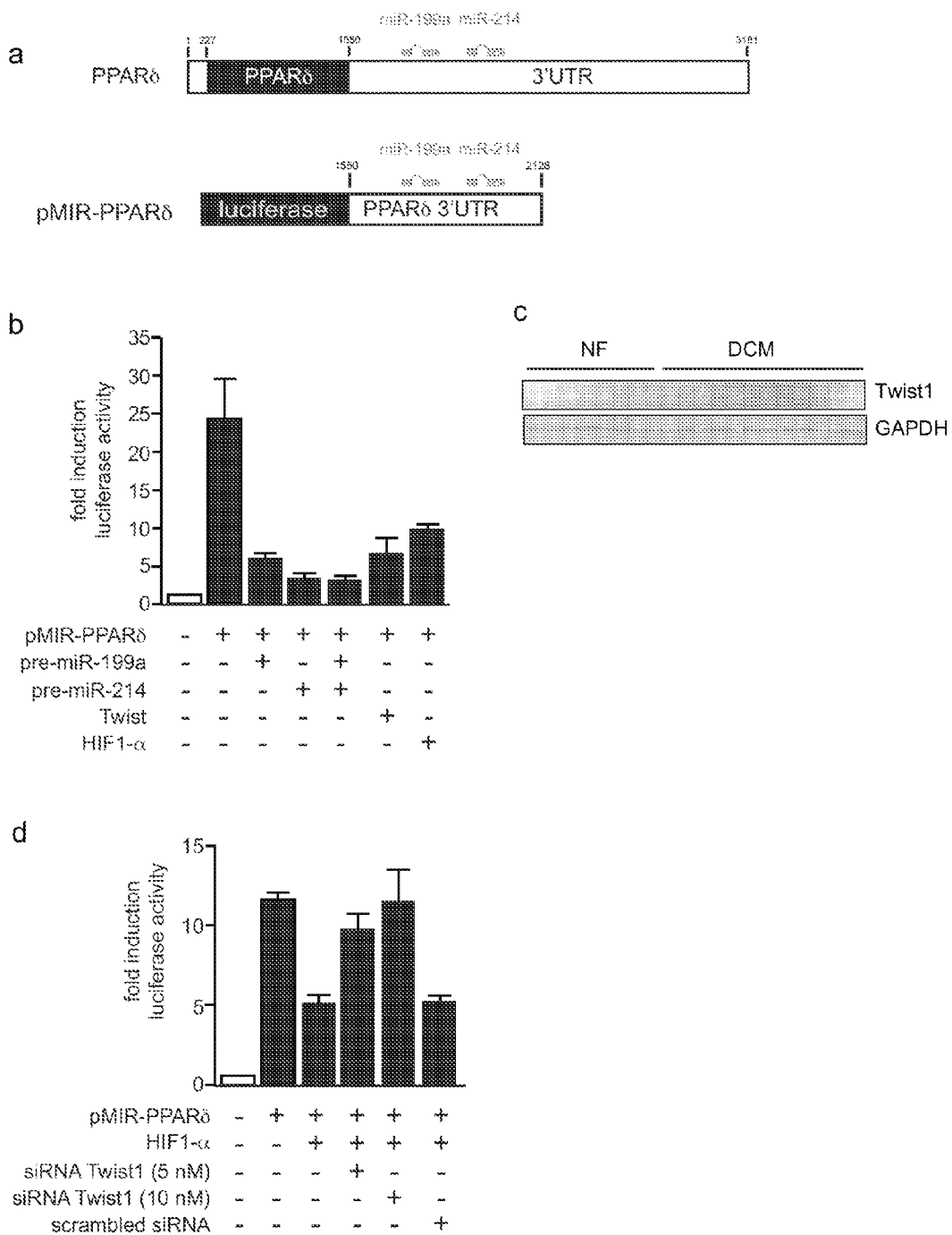
FIG. 2. PPARδ is a direct target for miR-199a-2 and miR-214. (A) Creation of a luciferase reporter (pMIR-PPARδ) that measures miR-199a/miR-214 sensitivity of the 3'UTR of PPARδ. (B) Expression of pMIR-PPARδ shows sensitivity to co-transfection with precursors for miR-199a-2, miR-214, Twist1 or HIF-1a. (C) HIF-1αsensitivity of pMIR-PPARδ was dependent upon the expression of Twist1, since siRNA-mediated knockdown abrogated the HIF-1αeffects. Error bars are mean±SEM of n=3.

To more directly confirm whether PPARδ is a direct target gene of this microRNA cluster, we made use of a miRNA expression reporter vector (pMiR-reporter, Ambion). This vector contains firefly luciferase under the control of the CMV mammalian promoter. The vector contains a multiple cloning site for insertion of a 3'UTR of predicted miRNA binding targets or other nucleotide sequences. By cloning the 3'UTR region of PPARδ, to which miR-199a-2/miR-214 are predicted to bind (FIG. 2, Panel a) into the pMiR-REPORT vector, the luciferase reporter will be subjected to regulation that will mimic regulation of the microRNA target (in this case, PPARδ). If overexpression of miR-199a/miR-214 would result in a decrease in luciferase activity, this provides strong evidence that the 3'UTR sequence of PPARδ is a direct target of these microRNAs. To this end, we cloned a region encompassing nucleotide 1598-2198 of murine PPARδ cDNA downstream of luciferase. Upon co-transfection of the pMiR-3'UTR-PPARδ luciferase reporter with precursor molecules for miR-199a-2 or miR-214, luciferase activity was strongly inhibited in the cells overexpressing either miR-199a-2 or miR-214, compared to the cells that were left untreated (FIG. 2, Panel b).

Since it was reported that dnm3os, the opposite strand of the dnm3 gene encoding the miR-199a-2/miR-214 cluster, was induced by the transcription factor Twist1, we tested whether Twist1 co-transfection (and concomitant induction of this microRNA cluster) with the pMiR-3'UTR-PPARδ luciferase reporter would suffice to down-regulate the luciferase reporter. Indeed, we observed a very similar down-regulation of the luciferase reporter as with precursor molecules for either microRNA alone (FIG. 2, Panel b). Twist1 was reported to be induced under hypoxic conditions by hypoxia-inducible factor-1 alpha (HIF-1α).[4] We tested whether the pMiR-3'UTR-PPARδ luciferase reporter was sensitive for HIF-1α induction. To this end, the pMiR-3'UTR-PPARδ luciferase reporter was co-transfected with an expression vector for HIF-1α. Again, a very similar down-regulation of the pMiR-3'UTR-PPARδ luciferase reporter was observed.

To establish whether the HIF-1α observed effects were directly dependent upon Twist1 induction, we next co-transfected the expression vector for HIF-1α with the pMiR-3'UTR-PPARδ luciferase reporter in the presence or absence of a short interfering RNA (siRNA) specific for Twist1. In the latter case, the HIF-1α-dependent down-regulation of the pMiR-3'UTR-PPARδ luciferase reporter was completely nullified, demonstrating the absolute requirement of Twist1 for the HIF-1α-dependent effects.

Taken together, these data show for the first time, that the miR-199a-2/miR-214 cluster plays an important role in regulating the expression of PPARδ, and that this cluster becomes induced following hypoxic conditions, given that PPARδ mRNA stability/translational efficiency was affected by a HIF-1α Twist1-dependent intracellular signaling pathway.

Deletion of PPARδ Causes Rapid Biventricular Dilation and Premature Death.

To investigate whether PPARδ gene activation is required for normal myocardial homeostasis and to bypass the early embryonic lethality of PPARδ-null mice, we first provoked deletion of a floxed PPARδ (ppard$^{f/f}$) allele using a tamoxifen-inducible Cre recombinase protein fused to two mutant estrogen-receptor ligand-binding domains under control of the cardiac-specific α-myosin heavy chain promoter.

We treated adult αMHC-MCM/ppard$^{f/f}$ and ppard$^{f/f}$ mice with vehicle or tamoxifen at the age of eight weeks. We noted that within five days of the start of tamoxifen delivery, αMHC-MCM/ppard$^{f/f}$ mice displayed a weak condition and inactivity, compared to tamoxifen-treated ppard$^{f/f}$, or vehicle-treated αMHC-MCM/ppard$^{f/f}$ control mice. Indeed, up to 25% of tamoxifen-treated αMHC-MCM/ppard$^{f/f}$ mice died within one week after starting of treatment and this mortality rate increased up to 75% during the following two weeks (data not shown).

Figure 3:
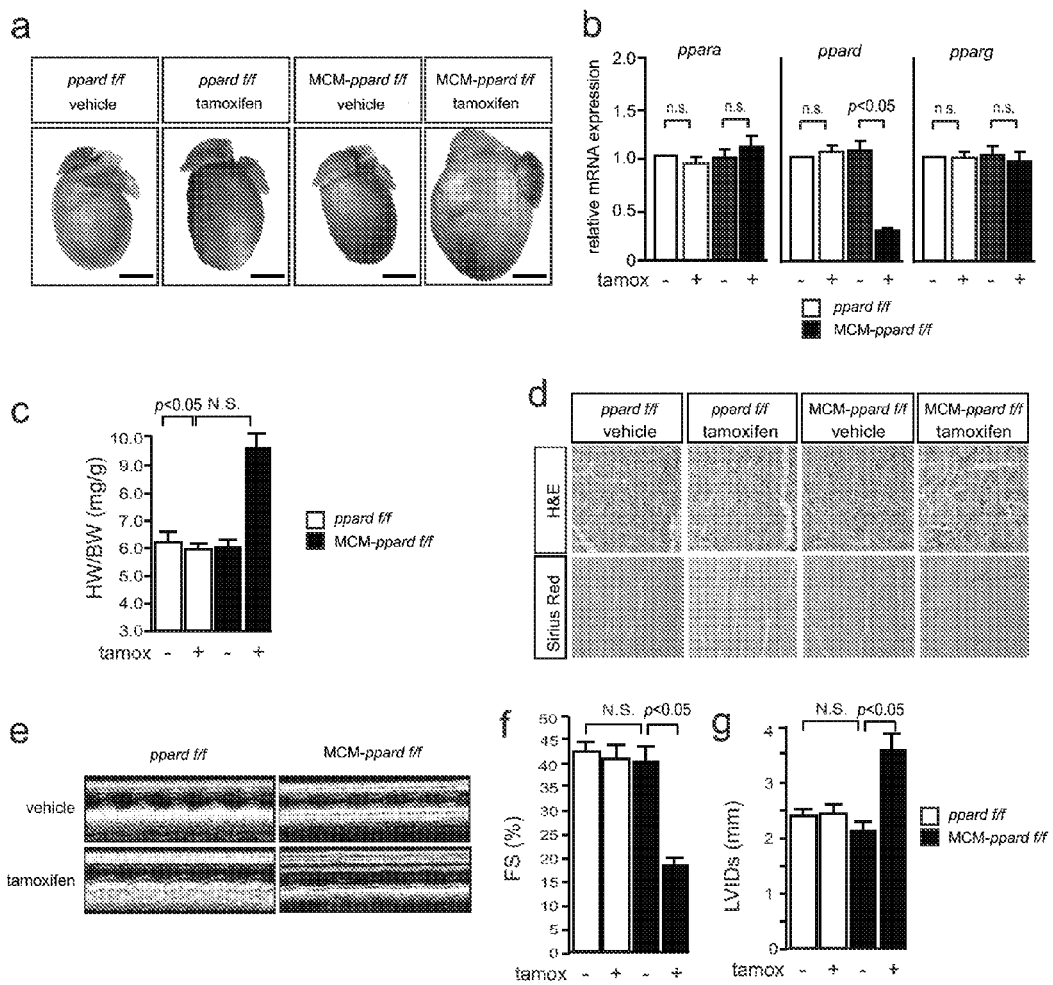
FIG. 3. Deletion of PPARδ provokes spontaneous cardiac remodeling. (A) Representative gross morphology of hearts dissected from eight-week-old mice of indicated genotypes, demonstrating visible cardiac enlargement by ppard deletion in the adult mouse heart (bar 5 mm) (B) Real-time PCR analysis of endogenous transcripts of ppara, ppard and pparg in the indicated genotypes, indicating specific deletion of endogenous ppard transcripts in the heart following tamoxifen treatment of MHC-MCM-ppard$^{f/f}$ mice. (C) Heart weight to body weight ratio in the indicated genotypes indicates hypertrophic remodeling in MHC-MCM-ppard$^{f/f}$ mice after tamoxifen treatment. (D) Representative histological images of hearts from mice with indicated genotypes (bar 2 mm) Sirius red staining indicates massive interstitial and perivascular fibrosis in hearts of MHC-MCM-ppard$^{f/f}$ mice after tamoxifen treatment. (E) Representative M-mode images of mice with indicated genotypes. (F) Bar graph representation of Fractional Shortening (FS) in indicated genotypes indicates loss of contractility in hearts of MHC-MCM-ppard$^{f/f}$ mice after tamoxifen treatment (n=6 per group). (G) Bar graph representation of ejection fraction (EF) in indicated genotypes indicates loss of cardiac output in hearts of MHC-MCM-ppard$^{f/f}$ mice after tamoxifen treatment (n=6 per group).

In addition, hearts from tamoxifen-treated αMHC-MCM/ppard$^{f/f}$ mice displayed doubling in heart weight compared to their control littermates (FIG. 3, Panel a). To ascertain whether we indeed created mice with deficiency for ppard, we performed real time RT-PCR for all three endogenous PPAR isoforms. The data show that our genetic intervention did not intervene with ppara or pparg transcripts, but specifically induced strong down-regulation of ppard transcripts (FIG. 3, Panel b).

A severe histopathology was evident after staining histological sections with H&E and Sirius Red. Cardiac tissue revealed an intricate phenotype with hypertrophied myofibers, myocyte disarray, strong inflammatory infiltration and interstitial fibrosis (FIG. 3, Panel d), hallmark features observed in experimental and clinical heart failure biopsies. Sirius red staining indicated massive interstitial and perivascular fibrosis in hearts from tamoxifen-treated αMHC-MCM/ppard$^{f/f}$ mice (FIG. 3, Panel d).

Furthermore, measurements of heart-weight-to-body-weight (HW/BW) ratios indicated a similar increase in cardiac mass for tamoxifen-treated αMHC-MCM/ppard$^{f/f}$ mice (7.5±1.2 mg/g) compared to tamoxifen-treated ppard$^{f/f}$ (6.2±0.9 mg/g) (FIG. 3, Panel c). These data demonstrate that adult-onset, cardiac-specific deletion of PPARδ causes rapid cardiac remodeling, reduced survivability and multiple signs of end-stage heart failure.

Targeted Deletion of PPARδ in the Adult Heart Causes Severe Cardiac Dysfunction and Induction of Fetal Genes.

Cardiac geometry and function was assessed non-invasively by echocardiography at two weeks after tamoxifen treatment (FIG. 3). After two weeks, vehicle-treated ppard$^{f/f}$ and αMHC-MCM/ppard$^{f/f}$ mice demonstrated normal cardiac geometry and function as indicated by fractional shortening (FS) (FIG. 3, Panel e), left ventricular internal dimensions (LVID) and left ventricular mass (FIG. 3, Panel e). As expected, tamoxifen-treated ppard$^{f/f}$ mice showed no alterations in FS or other parameters. In contrast, at two weeks, αMHC-MCM/ppard$^{f/f}$ animals demonstrated a rapid and significant decline in cardiac function, indicated by a 50% decrease in FS ($P<0.05$; FIG. 3, Panel f). At this time point after tamoxifen treatment, αMHC-MCM/ppard$^{f/f}$ mice also showed a more pronounced deterioration in cardiac geometry compared to vehicle-treated αMHC-MCM/ppard$^{f/f}$ mice, as demonstrated by an increase of 80-90% in LV internal diameters (LVIDs; FIG. 3, Panel g), indicating a rapid dilation of the left ventricle. These data demonstrate that PPARδ depletion provokes progressive functional and geometrical deterioration consistent with a heart failure phenotype.

Figure 4:
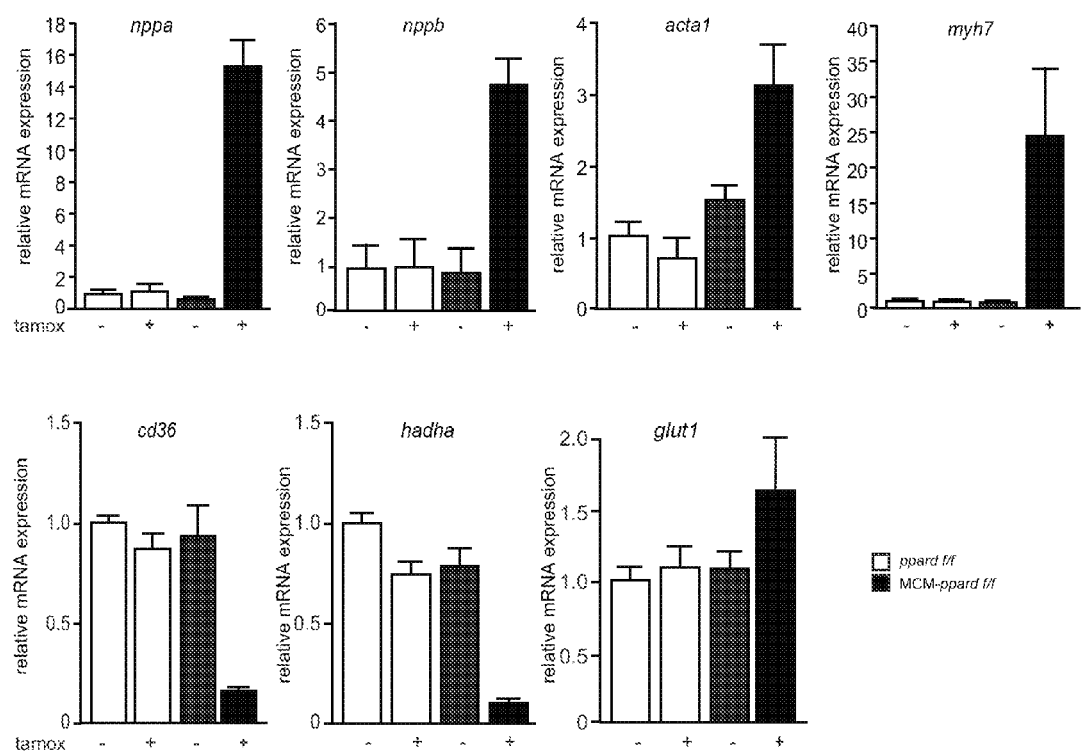
FIG. 4. Targeted deletion of PPARδ in the adult heart increases the expression of fetal and glycolytic genes, and decreases expression of fatty acid transport and oxidation genes. Analysis of expression of transcripts for several fetal genes indicative of heart failure (nppa, nppb, myh7 and acta1), glut1 (indicative of the rate of glycolysis), cd36 and hadha (indicative of fatty acid transport and oxidation) by quantitative real time PCR in ventricular tissue of indicated genotypes. Error bars are mean±SEM of n=3.
Figure 5:
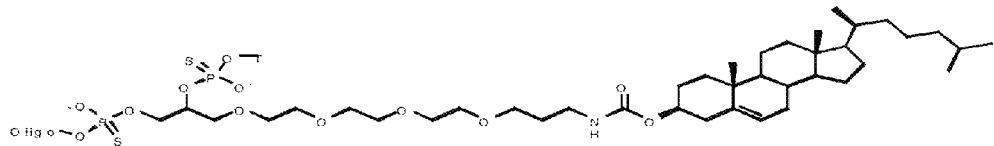
FIG. 5. Chemical composition of antagomirs against miR-199a-2 and miR-214. (A) Non-limiting example of a nucleotide sequence capable of inhibiting miR-199a-2 or (B) miR-214. Sequences shown in (A) include hsa-miR-199a-5p (SEQ ID NO:1) and an antagomir capable of blocking hsa-miR-199a (SEQ ID NO:18). Sequences shown in (B) include hsa-miR-214 (SEQ ID NO:3) and an antagomir capable of blocking hsa-miR-214 (SEQ ID NO:19). Oligo description (antagomir): 20-23 nt long, all 2'-Ome, 3'-cholesterol modification of Type 1, 5-7 PS bonds, PAGE or HPLC purified.
Figure 5:
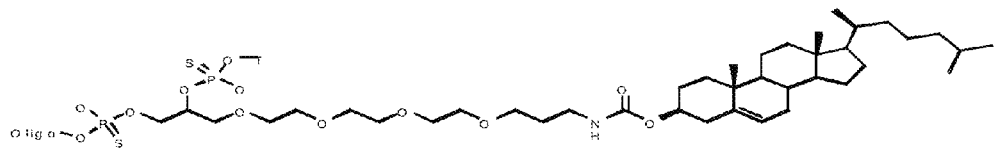

Deletion of PPARδ in adult mice also induced potent reactivation of embryonic genes such as acta1, nppb, myh7 and nppa in eight-week-old αMHC-MCM/ppard$^{f/f}$ hearts (FIG. 4). There was no substantial change in the expression of any of these genes in hearts of tamoxifen- or vehicle-treated control genotypes. Moreover, we noted a substantial decrease in transcript abundance for cd36 and hadha, and an increase in glut1 (FIG. 4). These data are indicative for a reduction in fatty acid transport capacity and oxidation, and a concomitant increase in glycolysis. Conclusively, deletion of PPARδ in the adult heart induces rapid and spontaneous cardiac dysfunction with strong induction of "fetal" hypertrophic marker genes.

REFERENCES

1. Sohal D. S., M. Nghiem, M. A. Crackower, et al. Temporally regulated and tissue-specific gene manipulations in the adult and embryonic heart using a tamoxifen-inducible Cre protein. *Circ. Res.* 2001; 89(1):20-25.
2. van Rooij E., P. A. Doevendans, H. J. Crijns, et al. MCIP1 overexpression suppresses left ventricular remodeling and sustains cardiac function after myocardial infarction. *Circ. Res.* 2004; 94(3):e18-26.
3. Lee Y. B., I. Bantounas, D. Y. Lee, et al. Twist-1 regulates the miR-199a/214 cluster during development. *Nucleic Acids Res.* 2009; 37(1):123-128.
4. Yang M. H., M. Z. Wu, S. H. Chiou, et al. Direct regulation of TWIST by HIF-1alpha promotes metastasis. *Nat. Cell Biol.* 2008; 10(3):295-305.
5. Van Rooij E., P. A. Doevendans, C. C. De Theije, F. A. Babiker, J. D. Molkentin, and L. J. De Windt. Requirement of nuclear factor of activated T-cells in calcineurin-mediated cardiomyocyte hypertrophy. *J. Biol. Chem.* 2002; 50:48617-48626.
6. De Windt L. J., H. W. Lim, S. Haq, T. Force, and J. D. Molkentin. Calcineurin promotes protein kinase C and c-Jun NH2-terminal kinase activation in the heart. Crosstalk between cardiac hypertrophic signaling pathways. *J. Biol. Chem.* 2000; 275(18):13571-13579.
7. Bernstein E., A. A. Caudy, S. M. Hammond, and G. J. Hannon. Role for a bidentate ribonuclease in the initiation step of RNA interference. *Nature* 2001; 409(6818): 363-366.

What is claimed is:

1. A method for modulating peroxisome proliferator activator receptor delta (PPARδ) expression levels in a cardiac muscle target cell, comprising: administering a microRNA (miR) antagonist to the target cell in an amount sufficient to modulate PPARδ levels, said miR antagonist comprising a modified oligonucleotide consisting of 15 to 20 linked nucleosides, wherein the nucleobase sequence of the modified oligonucleotide is complementary to a sequence at least 90% identical to the miR selected from the group consisting of SEQ ID NO: 3 (miR-214), SEQ ID NO: 1 (miR-199a-5p), SEQ ID NO:2 (miR-199a-3p) and SEQ ID NO:4 (miR-214*), and wherein PPARδ levels are increased or restored after administration.

2. The method of claim 1, wherein the nucleobase sequence of the modified oligonucleotide is identical to a sequence fully complimentary to the miR.

3. The method of claim 1, wherein administering a miR antagonist comprises: administering an antisense miR expression vector to a target cells and expressing an antisense miR in the target cells.

4. The method of claim 1, comprising contacting the target cell with an antisense miR-214 inhibitory RNA, and wherein PPARδ levels are increased or restored after administration.

5. The method of claim 1, comprising contacting the target cell with an antisense miR-199a-5p inhibitory RNA, and wherein PPARδ levels are increased or restored after administration.

6. The method of claim 1, comprising contacting the target cell with an antisense miR-199a-3p inhibitory RNA, and wherein PPARδ levels are increased or restored after administration.

7. The method of claim 1, comprising contacting the target cell with an antisense miR-214* inhibitory RNA, and wherein PPARδ levels are increased or restored after administration.

* * * * *